United States Patent
Hussain et al.

(10) Patent No.: US 9,693,841 B2
(45) Date of Patent: Jul. 4, 2017

(54) SURFACE TREATED STAPLES, SUTURES AND DENTAL FLOSS AND METHODS OF MANUFACTURING THE SAME

(71) Applicants: Ali Hussain, Cape Coral, FL (US);
Linda Cahalan, Cape Coral, FL (US);
Greg Johnson, Pittsburgh, PA (US);
Mark Gartner, Wexford, PA (US);
Patrick Cahalan, Cape Coral, FL (US);
Brian J Fill, Pittsburgh, PA (US);
Jeffrey W. Speakman, Saxonburg, PA (US)

(72) Inventors: Ali Hussain, Cape Coral, FL (US);
Linda Cahalan, Cape Coral, FL (US);
Greg Johnson, Pittsburgh, PA (US);
Mark Gartner, Wexford, PA (US);
Patrick Cahalan, Cape Coral, FL (US);
Brian J Fill, Pittsburgh, PA (US);
Jeffrey W. Speakman, Saxonburg, PA (US)

(73) Assignee: ENSION, INC., Pittsburgh, PA (US)

( * ) Notice: Subject to any disclaimer, the term of this patent is extended or adjusted under 35 U.S.C. 154(b) by 183 days.

(21) Appl. No.: 14/214,248

(22) Filed: Mar. 14, 2014

(65) Prior Publication Data
US 2014/0288592 A1 Sep. 25, 2014

Related U.S. Application Data

(63) Continuation-in-part of application No. 13/632,197, filed on Oct. 1, 2012, which is a continuation-in-part
(Continued)

(51) Int. Cl.
*A61C 15/04* (2006.01)
*A61B 17/06* (2006.01)
(Continued)

(52) U.S. Cl.
CPC .......... *A61C 15/041* (2013.01); *A61B 17/064* (2013.01); *A61B 17/06166* (2013.01);
(Continued)

(58) Field of Classification Search
CPC .......... A61K 9/70; A61B 17/06; A61B 17/04; C07K 14/78; B05D 3/06
(Continued)

(56) References Cited

U.S. PATENT DOCUMENTS 2,493,943 A 1/1950 Bower
2,615,450 A 10/1952 Bower
(Continued)

FOREIGN PATENT DOCUMENTS

EP 0 262 890 4/1988
EP 0 372 969 6/1990
(Continued)

*Primary Examiner* — Dah-Wei D Yuan
*Assistant Examiner* — Andrew Bowman
(74) *Attorney, Agent, or Firm* — Blynn L. Shideler; Krisanne Shideler; BLK Law Group

(57) ABSTRACT

A variety of medical devices including staples sutures and dental floss with surface treatment on at least one tissue-facing surface to improve biologic function such as to control tissue adhesion are disclosed including heparin surface treatment which provides heparin present in an amount to yield heparin bioactivity of at least one of i) an ATIII binding of at least 2 pmol/cm$^2$, and ii) a thrombin deactivation of at least 0.2 IU/cm$^2$; an acrylic surface treatment for coupling thereto of a heparin surface treatment, a collagen surface treatment or both; and an amino-functional polysiloxane surface treatment for coupling thereto of a heparin surface treatment.

7 Claims, 7 Drawing Sheets

Related U.S. Application Data of application No. 13/345,813, filed on Jan. 9, 2012, now Pat. No. 8,343,567, which is a continuation of application No. 12/061,212, filed on Apr. 2, 2008, now Pat. No. 8,114,465.

(60) Provisional application No. 61/788,092, filed on Mar. 15, 2013, provisional application No. 60/909,553, filed on Apr. 2, 2007, provisional application No. 61/551,619, filed on Oct. 26, 2011.

(51) Int. Cl.
| | | |
|---|---|---|
| *A61B 17/064* | (2006.01) | |
| *A61L 31/04* | (2006.01) | |
| *A61L 31/10* | (2006.01) | |
| *A61L 33/00* | (2006.01) | |
| *B05D 3/06* | (2006.01) | |
| *A61M 1/16* | (2006.01) | |
| *B05D 7/02* | (2006.01) | |
| *B05D 1/36* | (2006.01) | |
| *B05D 1/00* | (2006.01) | |

(52) U.S. Cl.
CPC ............ *A61L 31/048* (2013.01); *A61L 31/10* (2013.01); *A61L 33/0029* (2013.01); *A61B 17/06* (2013.01); *A61L 2400/18* (2013.01); *A61M 1/1698* (2013.01); *B05D 1/36* (2013.01); *B05D 1/62* (2013.01); *B05D 3/06* (2013.01); *B05D 7/02* (2013.01); *B05D 2256/00* (2013.01); *B05D 2258/00* (2013.01)

(58) Field of Classification Search
USPC .......... 424/443, 185.1, 198.1, 192.1, 195.11, 424/425, 426; 206/63.3; 606/213; 427/2.31
See application file for complete search history.

(56) References Cited

U.S. PATENT DOCUMENTS

| | | | |
|---|---|---|---|
| 3,896,814 A | 7/1975 | Vivien et al. | |
| 3,905,823 A | 9/1975 | Piskoti | |
| 3,980,177 A * | 9/1976 | McGregor | A61B 17/06004 206/63.3 |
| 4,027,676 A | 6/1977 | Mattei | |
| 4,043,344 A | 8/1977 | Landi et al. | |
| 4,047,533 A | 9/1977 | Perciaccante et al. | |
| 4,080,969 A | 3/1978 | Casey et al. | |
| 4,613,665 A | 9/1986 | Larm | |
| 4,649,920 A | 3/1987 | Rhum | |
| 4,705,820 A | 11/1987 | Wang et al. | |
| 4,840,626 A | 6/1989 | Linsky et al. | |
| 4,844,067 A | 7/1989 | Ikada et al. | |
| 4,975,247 A | 12/1990 | Badolato et al. | |
| 5,002,551 A | 3/1991 | Linsky et al. | |
| 5,032,638 A | 7/1991 | Wang et al. | |
| 5,049,403 A | 9/1991 | Larm et al. | |
| 5,077,372 A | 12/1991 | Hu et al. | |
| 5,089,013 A | 2/1992 | Bezwada et al. | |
| 5,100,433 A | 3/1992 | Bezwada et al. | |
| 5,102,420 A | 4/1992 | Hunter et al. | |
| 5,112,457 A | 5/1992 | Marchant | |
| 5,123,912 A | 6/1992 | Kaplan et al. | |
| 5,147,383 A | 9/1992 | Bezwada et al. | |
| 5,182,317 A | 1/1993 | Winters et al. | |
| 5,395,468 A | 3/1995 | Juliar et al. | |
| 5,593,441 A | 1/1997 | Lichtenstein et al. | |
| 5,716,376 A | 2/1998 | Roby et al. | |
| 5,795,584 A | 8/1998 | Totakura et al. | |
| 5,811,151 A | 9/1998 | Hendriks et al. | |
| 5,939,191 A | 8/1999 | Bennett et al. | |
| 6,024,918 A | 2/2000 | Hendriks et al. | |
| 6,270,788 B1 | 8/2001 | Koulik et al. | |
| 6,322,580 B1 * | 11/2001 | Kanner | A61B 17/0057 606/213 |
| 6,379,691 B1 | 4/2002 | Tedeschi et al. | |
| 6,436,481 B1 | 8/2002 | Chabrecek et al. | |
| 6,461,665 B1 | 10/2002 | Scholander | |
| 6,482,410 B1 * | 11/2002 | Crossin | C07K 14/47 424/185.1 |
| 6,497,650 B1 | 12/2002 | Nicolo | |
| 6,509,104 B2 | 1/2003 | Huang et al. | |
| 6,559,132 B1 | 5/2003 | Holmer | |
| 6,632,470 B2 | 10/2003 | Morra et al. | |
| 6,689,153 B1 | 2/2004 | Skiba | |
| 6,723,709 B1 | 4/2004 | Pressato et al. | |
| 6,756,125 B2 | 6/2004 | Al-Lamee | |
| 6,830,583 B2 | 12/2004 | Shah et al. | |
| 6,878,757 B2 | 4/2005 | Roby | |
| 6,921,811 B2 | 7/2005 | Zamora et al. | |
| 6,969,400 B2 | 11/2005 | Rhee et al. | |
| 7,034,061 B1 | 4/2006 | Luthra et al. | |
| 7,129,224 B1 | 10/2006 | Byun et al. | |
| RE39,438 E | 12/2006 | Shah et al. | |
| 7,154,804 B2 | 12/2006 | Takazawa et al. | |
| 7,172,765 B2 | 2/2007 | Chu et al. | |
| 7,294,357 B2 * | 11/2007 | Roby | A61L 17/145 427/2.31 |
| 7,749,204 B2 | 7/2010 | Dhanaraj et al. | |
| 7,767,726 B2 | 8/2010 | Sutermeister et al. | |
| 7,815,923 B2 | 10/2010 | Johnson et al. | |
| 7,829,133 B2 | 11/2010 | Vogt et al. | |
| 7,837,708 B2 | 11/2010 | Schmieding et al. | |
| 7,883,694 B2 | 2/2011 | Rhee et al. | |
| 7,897,171 B2 | 3/2011 | Strickler et al. | |
| 7,901,726 B2 | 3/2011 | McMorrow et al. | |
| 7,914,806 B2 | 3/2011 | Strickler et al. | |
| 7,914,807 B2 | 3/2011 | Brito et al. | |
| 7,919,137 B2 | 4/2011 | Sutermeister et al. | |
| 7,935,773 B2 | 5/2011 | Hadba et al. | |
| 8,012,173 B2 | 9/2011 | Vogt et al. | |
| 8,114,465 B2 | 2/2012 | Cahalan et al. | |
| 8,343,567 B2 | 1/2013 | Cahalan et al. | |
| 2005/0058692 A1 * | 3/2005 | Hai-Quan | A61K 47/482 424/443 |
| 2006/0246291 A1 | 11/2006 | Kunz et al. | |
| 2006/0286289 A1 | 12/2006 | Prajapati et al. | |
| 2008/0317810 A1 | 12/2008 | Sidhu et al. | |

FOREIGN PATENT DOCUMENTS

| | | |
|---|---|---|
| WO | 9735533 | 10/1997 |
| WO | 2005033219 | 5/2005 |
| WO | 2005082434 | 9/2005 |

* cited by examiner

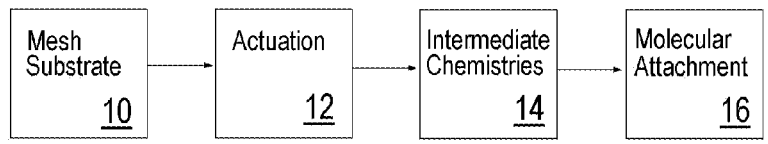
Figure 1
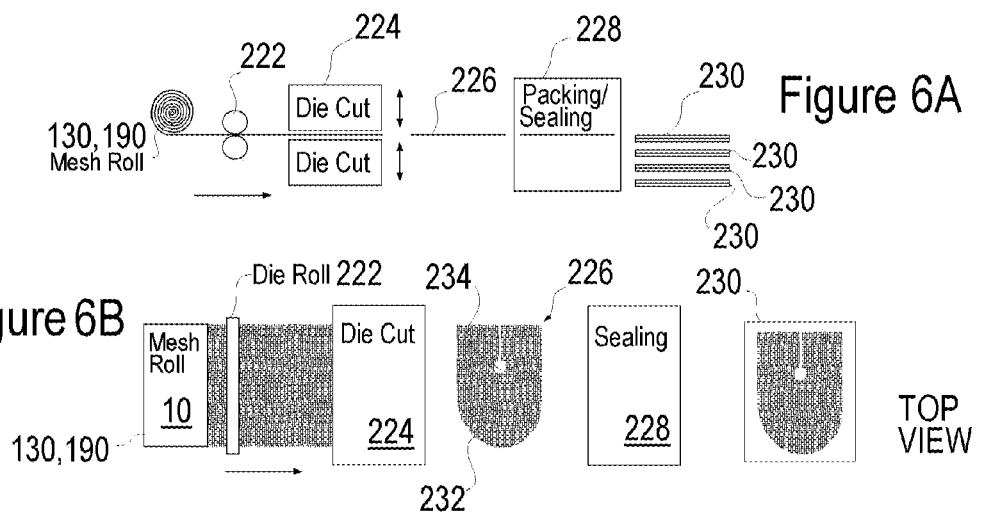
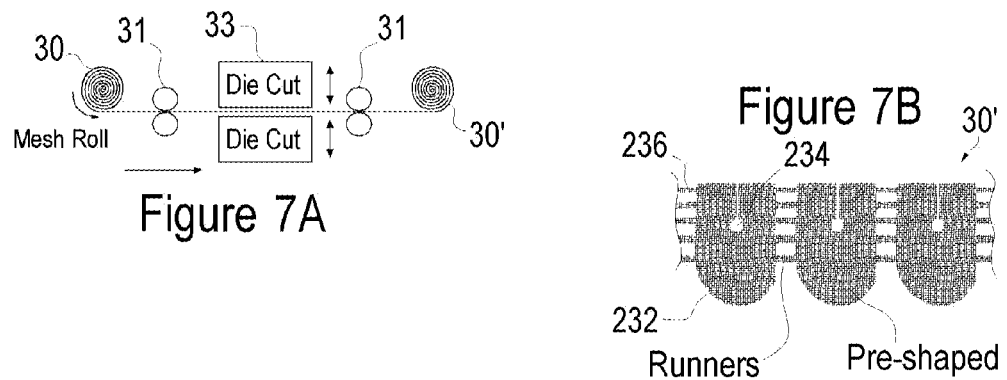
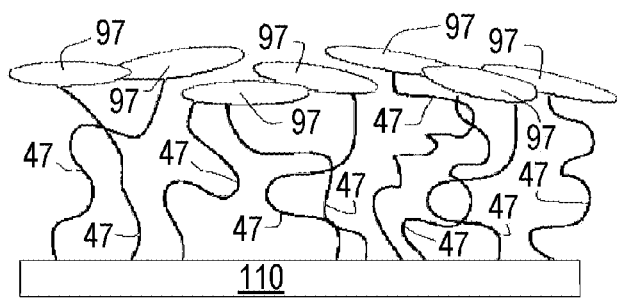
Figure 8

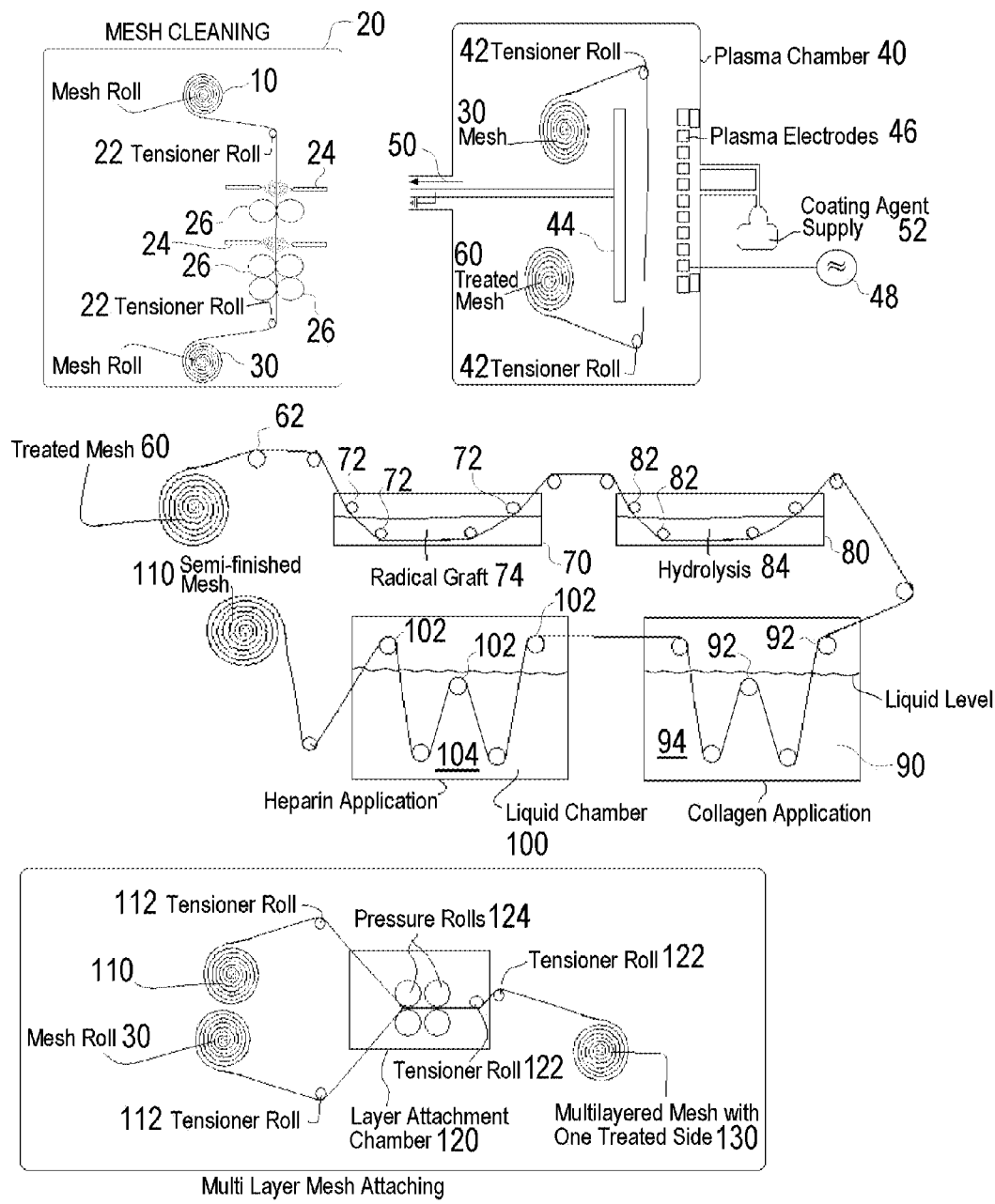
Figure 2 (PP/PE - Collagen - Heparin)

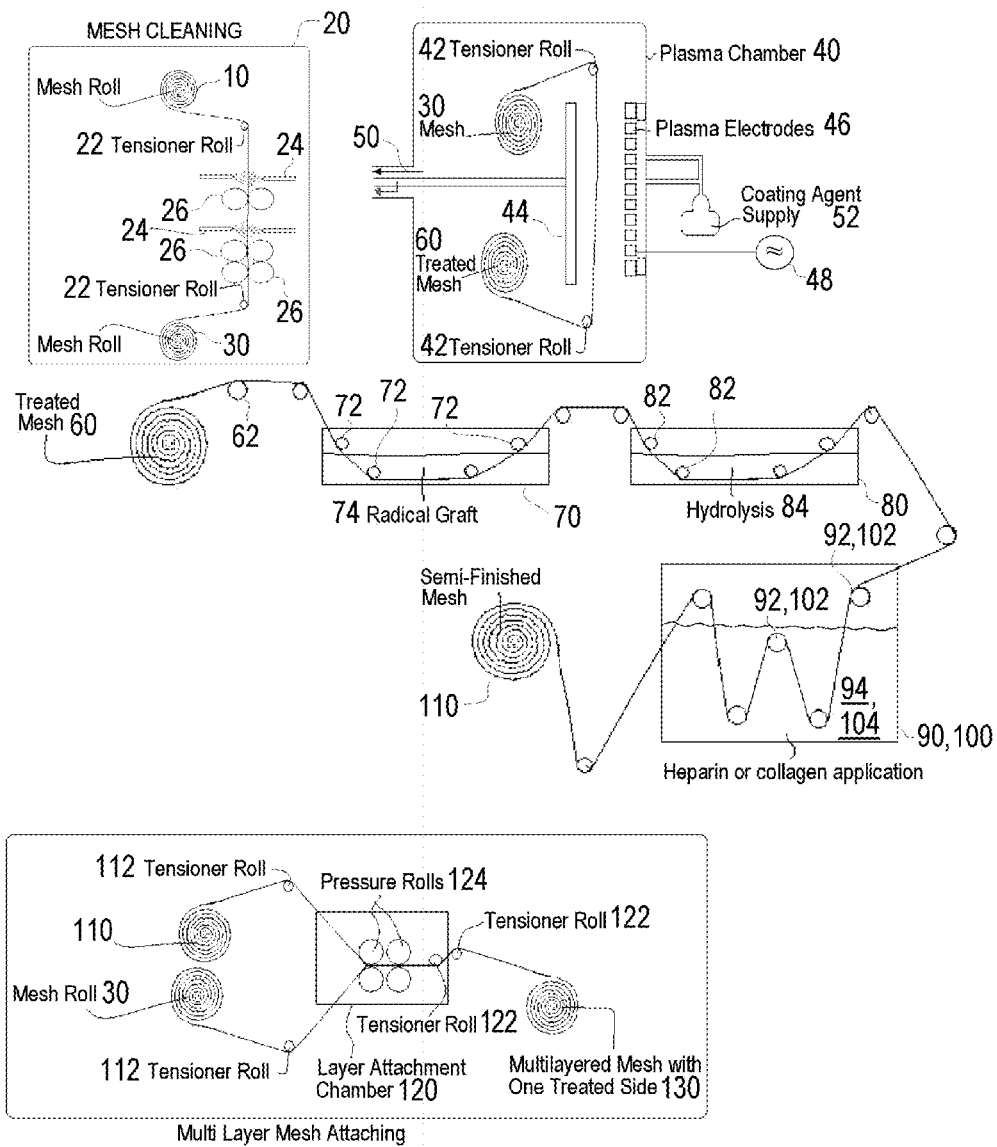

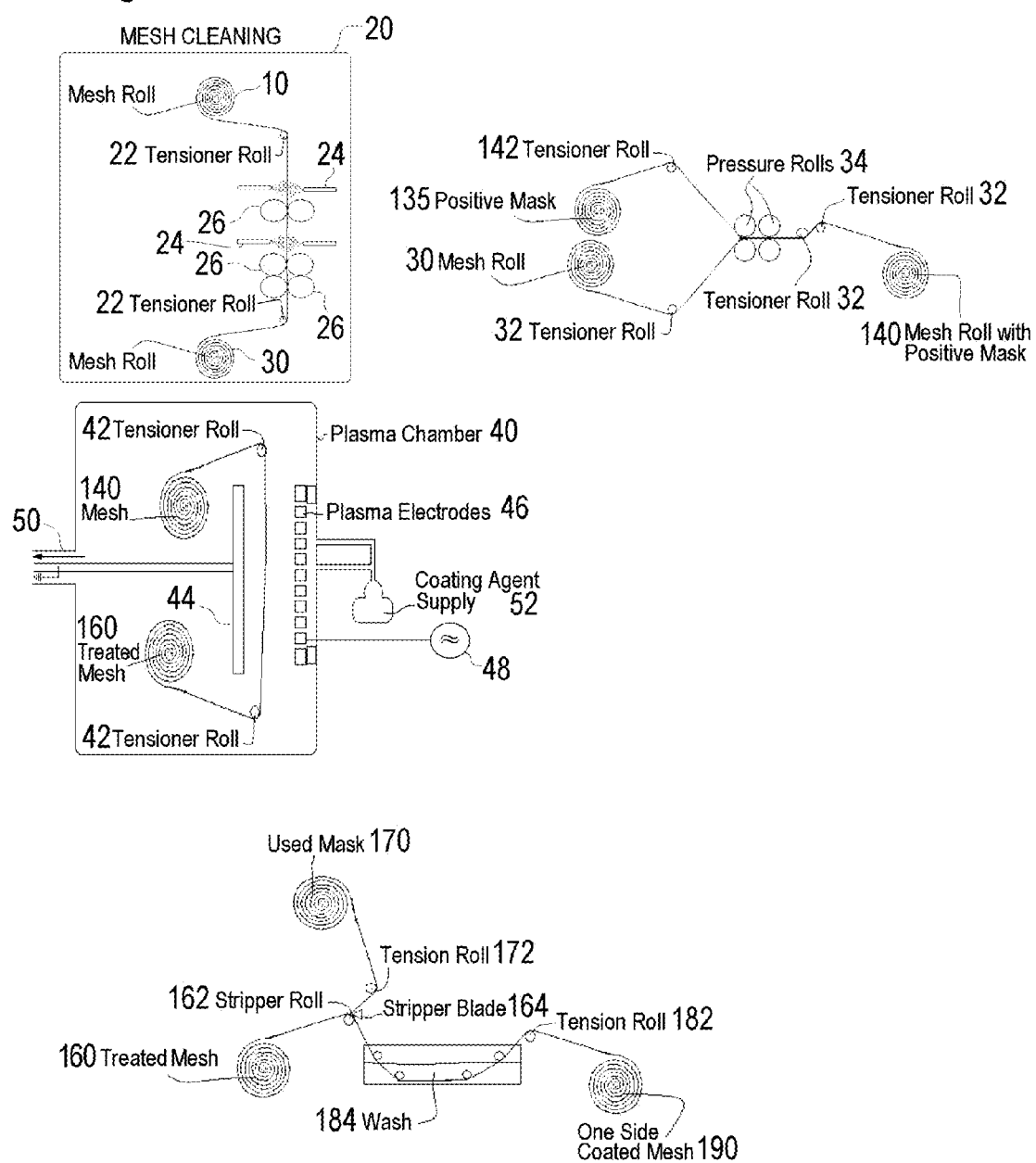

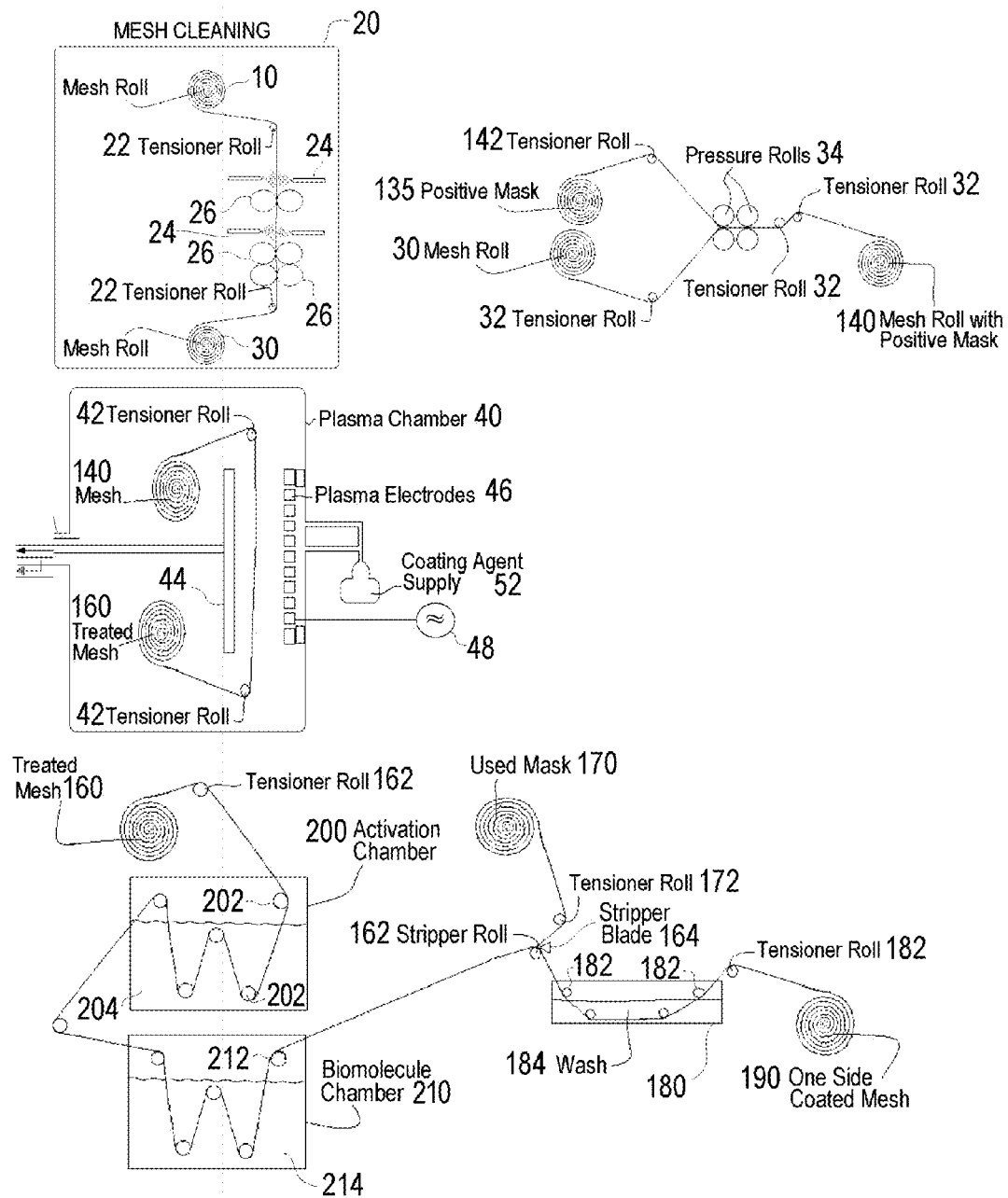
FIGURE 5 (PP/PE- siloxane-heparin via positive masking)

SURFACE TREATED STAPLES, SUTURES AND DENTAL FLOSS AND METHODS OF MANUFACTURING THE SAME

RELATED APPLICATIONS

This application claims priority to U.S. Provisional Patent Application Ser. No. 61/788,092 filed Mar. 15, 2013, entitled "Surface Treated Staples and Staples and Methods of Manufacturing the Same".

The present application is a continuation-in-part of U.S. patent application Ser. No. 13/632,197 filed Oct. 1, 2012 entitled "Surface Treated Polymeric Synthetic Hernia Mesh Prosthesis, Surface Treated Sutures and Staples and Methods of Manufacturing the Same" and which published as U.S. Patent Application Publication Number 2013-0110137 which publication is incorporated herein by reference.

U.S. patent application Ser. No. 13/632,197 claims priority to U.S. Provisional Patent Application Ser. No. 61/551,619 filed Oct. 26, 2011, entitled "Polymeric Synthetic Hernia Mesh Prosthesis with Surface Treatment to Control Tissue Adhesion."

U.S. patent application Ser. No. 13/632,197 is a continuation-in-part of U.S. patent application Ser. No. 13/345,813 filed Jan. 9, 2012 entitled "Method of Treating the Surface of a Medical Device with a Biomolecule" and which published as U.S. Patent Application Publication Number 2012-0107901, and issued as U.S. Pat. No. 8,343,567 and which publication and patent are incorporated herein by reference.

U.S. patent application Ser. No. 13/345,813 is a continuation of U.S. patent application Ser. No. 12/061,212 filed Apr. 2, 2008 entitled "Process for Preparing a Substrate Coated with a Biomolecule" and which published as U.S. Patent Application Publication Number 2008-0241349 and issued as U.S. Pat. No. 8,114,465, and which publication and patent are incorporated herein by reference.

U.S. patent application Ser. No. 12/061,212 claims the benefit of Provisional Patent Application Ser. No. 60/909,553 entitled "Process for Preparing a Substrate Coated with a Biomolecule" filed Apr. 2, 2007.

BACKGROUND OF THE INVENTION

Field of the Invention

The present invention relates to surface treated medical devices namely staples, dental floss and sutures and methods of forming the same.

Background Information

Medical Device Surface Treatment Background

Devices used in the medical field must be manufactured using materials, such as biomaterials, having particular surface properties so that the device functions without causing adverse effects to the patient.

Biomaterials are typically made of inert metals, polymers, or ceramics to ensure durability and to ensure that the materials do not adversely react with the physiological environment with which they come into contact, such as with blood or tissues. More particularly, many biomedical devices may or may not require blood compatible, infection resistant, and/or tissue compatible surfaces. For example, it is often desirable to manufacture medical devices, such as catheters, that have properties that discourage adherence of blood or tissue elements to the device.

It is also desirable for certain biomaterials, such as those for implants, to be anchored stably into the tissue environment into which they are implanted. For example, it may be desirable for specific implants, such as certain types of catheters and stents, to be non-inflammatory and anchored to the surrounding tissues. Moreover, it may be desirable for certain biomaterials to prevent bacterial growth during a course of a procedure, or as a permanent implant so as to prevent infection of a patient in contact with the biomaterial. Initial contact of such materials with blood may result in deposition of plasma proteins, such as albumin, fibrinogen, immunoglobulin, coagulation factors, and complement components. The adsorption of fibrinogen onto the surface of the material causes platelet adhesion, activation, and aggregation. Other cell adhesive proteins, such as fibronectin, vitronectin, and von Willebrand factor (vWF) also promote platelet adhesion.

In addition, disposable surgical tools may become infected with bacteria during a course of a long operation and reuse of the tool during the operation may promote bacterial infection in the patient. For certain tools used in particular applications, it may be desirable therefore to prevent any bacterial growth on the surfaces of these tools during the course of an operation.

Additionally for permanently implanted materials it would be desirable to prevent bacterial growth that would lead to a biomaterial or device centered infection. In the latter the only remedy is eventual removal of the implant.

Adverse reactions between materials and blood components are predominant factors limiting the use of synthetic materials that come into contact with physiological fluids.

A number of approaches have been suggested to improve the biocompatibility and blood compatibility of medical devices. One approach has been to modify the surface of the material to prevent undesirable protein adhesion by providing the material with a low polarity surface, a negatively charged surface, or a surface coated with biological materials, such as enzymes, endothelial cells, and proteins. Another approach has been to bind anticoagulants to the surface of biologically inert materials to impart antithrombogenic characteristics to the materials. Still another approach used in the art has been the copolymerization of various phospholipids which are used as coating materials for various substrates. Partial polymeric backbone coatings have also been used in a similar fashion. However, many of these methods can result in a leaching or "stripping off" of the coating.

In devices requiring the transfer of gases, for example, in blood oxygenators requiring the exchange of oxygen and carbon dioxide through a membrane or porous fiber, there are additional drawbacks. Often surfaces that have been rendered biocompatible by the coating of biomolecules attract phospholipids. Phospholipids that adhere to the surface coat the pores and wet the surface of the device, making it hydrophilic. Water adversely affects gas transfer, making the oxygenator significantly less effective.

There is a need in the art to develop processes for preparing substrates coated biomolecules that demonstrate biocompatibility and blood compatibility, while maintaining gas permeability.

Hernia Background

Hernias have plagued humans throughout recorded history, and descriptions of hernia reduction date back to Hammurabi of Babylon and early Egyptian writings. A hernia is usually a protrusion or sac formed by the lining of the abdominal cavity, the peritoneum. The hernia sac protrudes through the hernia defect, i.e. a hole or weak area, in the fascia. The fascia is the strong layer of the abdominal wall that surrounds the muscle. There are various types of hernias including ventral hernias, incisional hernias, inguinal hernias, hiatal hernias, femoral hernias, diaphragmatic hernias, diverticular hernias, barth hernias, epigastric hernias, interstitial hernias, sciatic hernias and umbilical hernias, defined largely by the location of the hernia defect. This is merely an illustrative and not a comprehensive listing of hernia classifications.

Surgery is essentially the only treatment that can permanently fix a hernia. Original hernia surgery utilized the patients existing tissue to repair the defect and this technique is now known as "pure tissue" repair of a hernia defect. Dr. Bassini has been noted as an early pioneer in successful pure tissue repair of hernias when in 1888 he reported a reduction in the recurrence rate of pure tissue hernia repair to about 10% (from a conservative estimated 30-40% rate earlier) with his procedure that combined an understanding of anatomy with an application of surgical thinking and surgical technique. This 10% recurrence rate is quite impressive when noted that it was achieved at a period without antibiotics, primitive anesthesia and at a time when patients often suffered with their hernia until they reached a giant size before submitting to surgery. For well over a century, Bassini's pure tissue repair procedures, with several modifications (e.g. Halsted, McVay, Tanner, and Shouldice) have helped preserve useful life in hundreds of thousands cases.

Hernia repair prosthetics have been developed, also called hernia repair patches, hernia repair fabrics and hernia repair meshes, for use in what is known as a tension free repair of a hernia defect. The hernia prosthetic generally plugs and/or bridges the gap forming the defect and the patient's tissue is not "stretched" over the defect, thus allowing the tissue to remain "tension free". The tension-free repair is invariably linked to Dr. Lichtenstein whose work and progress over two decades culminated in what is known as the tension free Lichtenstein repair. The precise amount of reoccurrence varies with the type of hernia and the associated procedure utilized, but in essentially all cases the "tension free" prosthetic repair substantially reduces reoccurrence of hernias over the pure tissue repair, a minimized recovery period. Further, tension free prosthetic hernia repair further yielded a decrease in post operative patient pain and thus has become the most popular repair for hernia defects.

Numerous surgically implantable hernia repair prosthetics have been proposed. Hernia repair mesh prosthesis formed of synthetic materials such as polypropylene (PP), polyester (PET), and polytetrafluoroethylene (PTFE), and combinations thereof are some of the most common. Within the meaning of this patent application the term mesh references a flexible fabric formed by a netting of filaments with mesh openings between the filaments forming an open texture. These synthetic prosthetics are generally intended for permanent placement within a patient's body space. Hernia repair mesh prosthesis formed of non-synthetic or biological materials have also been proposed, with some biological prostheses designed for permanent placement within a patient's body space and others designed for partial or complete absorption into the patient's body over time (hopefully after the hernia defect has been fully repaired).

In certain procedures, including incisional and umbilical hernia repair and chest reconstruction, the synthetic hernia repair prosthetic may come into direct contact with the sensitive abdominal viscera. Postoperative adhesions between the prosthesis and the intestine may occur, potentially leading to intestinal fistulization. Various approaches to reducing the incidence of postoperative adhesions arising from the use of prosthetic materials have been proposed by the prior art. It has further been suggested to cover the prosthesis with peritoneum or other tissue, where available or adequate to close the defect, to form a natural biological barrier between the implant and the bowel.

Also proposed has been the placement of a physical barrier between the surgical site and the surrounding tissue where adhesions are most commonly encountered. For example In an article entitled "Heparin Releasing Anti-adhesive Membranes" by Y. Noishiki and T. Miyata published in Jinko Zoki, 14(2), p. 788-79 1 (1985), a collagen membrane (special treated human amnion) having protamine cross-linked into the collagen network was immersed in 1% heparin solution so the heparin was ionically bound to the protamine which had been cross-linked in the collagen. The resultant heparinized collagen membrane was stitched into place covering a wound on the serosal membrane of the large intestines of dogs. The animals were examined after 3 days, 60 days, 173 days and 687 days. No signs of adhesions were found. These collagen membranes were not biodegradable, since much of these membranes remained even after 687 days. The heparin was released slowly and steadily, so that 76% of the heparin originally present in the membrane was released over a period of three months.

Jenkins et al., "A Comparison of Prosthetic Materials Used to Repair Abdominal Wall Defects", Surgery, Vol. 94, No. 2, August 1983, pg. 392-398, describes a technique of placing an absorbable gelatin film (GELFILM® brand) freely between a piece of MARLEX® brand knitted polypropylene monofilament mesh and the abdominal viscera. The gelatin film dissolved after one week. Thereafter, the incidence of adhesions was reported to be the same as with using the Marlex mesh alone.

U.S. Pat. No. 4,840,626 discloses a process of preventing post-surgical adhesions which comprises positioning as a physical barrier between the site of the surgical activity and neighboring tissue with a distinct physical barrier formed as a heparin-containing matrix of an oxidized regenerated cellulose adhesion-preventative barrier fabric. This patent also discloses the process of administering heparin topically to an internal body organ during surgery for the purpose of preventing surgical adhesions which comprises applying an oxidized regenerated cellulose fabric containing heparin absorbed on it to the outer surface of an internal body organ, with the fabric (or other matrix) being drapable, conformable, adherent to body organs, and substantially absorbable within thirty (30) days in the body.

U.S. Pat. No. 5,002,551 discloses a physical barrier formed of a knitted oxidized regenerated cellulose (referenced as "Intercede (TC7)"). The patent indicates that other physical barriers include silicone elastomers and absorbable gelatin films. Clinical studies of Intercede (TC7) were reported in "Prevention of Postsurgical Adhesions by Intercede (TC7), An Absorbable Adhesion Barrier: A Prospective, Randomized Multicenter Clinical Study", Fertility and Sterility, Vol. 51, No. 6, June 1989, pg. 93-938. Such physical barriers alone are not sufficient to reinforce the abdominal wall or to repair abdominal wall defects.

U.S. Pat. No. 5,077,372 discloses a medical device coated with an antithrombogenic agent, covalently linked to the amino groups of the polyurethane coating. These coating reactions and heparinizations are carried out directly on the device's surface. Such methods as disclosed herein, however, have been suggested to suffer from decreased bioactivity, and consequently, increased thrombogenicity.

U.S. Pat. No. 5,593,441 is a representative example of one synthetic polymeric hernia mesh prosthesis and discloses ventral hernia and/or chest wall reconstruction prosthesis that is a polypropylene mesh covered with an adhesion resistant barrier, such as a sheet of expanded PTFE. In the repair of ventral hernias and in chest wall reconstruction, the composite prosthesis is positioned with the barrier relative to the region of potential adhesion, such as the abdominal viscera. Similarly, International Publication No. WO 97/35533 proposed a composite prosthesis in which one side of a layer of mesh material is completely covered with a layer of barrier material. The mesh material promotes biological tissue in-growth while the barrier material retards biological tissue adherence thereto. PTFE, however, has yielded increased complications relating to treatment of postoperative infections.

U.S. Pat. No. 5,795,584 describes a post-surgical antiadhesion device further described as surgical adhesion barriers and methods of using such surgical adhesion barriers are provided. Surgical adhesion barriers according to the patent have at least one layer of a bioabsorbable material comprising copolymers and/or block copolymers derived from trimethylene carbonate. Alternatively, a multilayer surgical structure having one or more bioabsorbable layers superimposed on a non-absorbable layer is useful for minimizing or preventing formation of fibrous adhesions between a healing trauma site and adjacent surrounding tissue. Alternatively, a bioabsorbable nonwoven fabric in adherent contact with at least one bioabsorbable layer of foam, film, mesh, web or woven fabric is also provided. One or more medicinal agents may be interposed between or disposed within any of the aforementioned layers.

U.S. Pat. Nos. 6,497,650 and 7,154,804 also disclose prosthesis for repairing a tissue or muscle wall defect. The prosthesis comprises a layer of repair fabric having first and second and an edge that extends between the first and second surfaces. The prosthesis also includes a barrier that is inhibits the formation of adhesions with adjacent tissues and organs. The barrier may overlap a portion of the first and second surfaces. The barrier may be formed separate from and attached to the layer of repair fabric to permanently cover a portion of the edge. The repair fabric may be formed from a material which is susceptible to the formation of adhesions with sensitive tissue and organs. The cord protector may be formed from material which inhibits the formation of adhesions with sensitive tissue and organs. The barrier may overlie a portion of at least one of the first and second surfaces of the repair fabric.

U.S. Pat. No. 6,723,709 discloses biomaterials essentially constituted by esterified derivatives of hyaluronic acid or by cross-linked derivatives of hyaluronic acid for use in the surgical sector, particularly for use in the prevention of post-surgical adhesion.

U.S. Pat. No. 6,969,400 discloses a synthetic implant with nonimmunogenicity coating described as crosslinked polymer compositions that include a first synthetic polymer containing multiple nucleophilic groups covalently bound to a second synthetic polymer containing multiple electrophilic groups. The first synthetic polymer is preferably a synthetic polypeptide or a polyethylene glycol that has been modified to contain multiple nucleophilic groups, such as primary amino (—NH.sub.2) or thiol (—SH) groups. The second synthetic polymer may be a hydrophilic or hydrophobic synthetic polymer, which contains or has been derivatized to contain, two or more electrophilic groups, such as succinimidyl groups. The compositions may further include other components, such as naturally occurring polysaccharides or proteins (such as glycosaminoglycans or collagen) and/or biologically active agents. Also disclosed are methods for using the crosslinked polymer compositions to affect adhesion between a first surface and a second surface; to effect tissue augmentation; to prevent the formation of surgical adhesions; and to coat a surface of a synthetic implant.

U.S. Pat. No. 7,172,765 notes that other materials have also been used to form physical barriers in an attempt to prevent adhesions, including silicone elastomers, gelatin films and knit fabrics of oxidized regenerated cellulose (hereinafter ORC). In some cases This patent notes that it is suggested that heparin, heparinoid, or hexuronyl hexosaminogly can be incorporated into the matrix of an ORC fabric or other matrices of hyaluronic acid, cross-linked and uncross-linked collagen webs, synthetic resorbable polymers, gelatin films, absorbable gel films, oxidized cellulose fabrics and films which are fabricated into a form that is said to be drapable, conformable and adherent to body organs and substantially absorbable within 30 days. This patent references U.S. Pat. No. 4,840,626, EPA Publication No. 0 262 890 and EPA Publication No. 0 372 969 as examples of this point. However, this patent suggests it is difficult to precisely control the degradation rate of many of these materials and scar tissue can result from use of many of the materials.

U.S. Pat. No. 7,749,204 discloses a reinforced absorbable multilayered fabric for use in tissue repair and regeneration described as directed to a method of using a multilayered fabric comprising a first absorbable nonwoven fabric and a second absorbable woven or knitted fabric in tissue repair and regeneration. The patent adds that additionally, the reinforced absorbable multilayered fabric may contain bioactive agents to aid in the repair or regeneration of tissue. Examples of bioactive agents include cell attachment mediators, such as peptide-containing variations of the "RGD" integrin binding sequence known to affect cellular attachment, biologically active ligands, and substances that enhance or exclude particular varieties of cellular or tissue ingrowth.

U.S. Pat. No. 7,815,923 discloses an implantable graft material that is suitable for implantation within a patient including isolated tissue material remodeled in a body cavity. The patent states "In addition to being cross linked, the ECM material can be treated (e.g., brought into contact, impregnated, coated, etc.) with one or more desirable compositions, such as anticoagulants (e.g., heparin), growth factors, other desirable property modifiers, and the like to modify the tissue properties."

U.S. Pat. No. 7,883,694 discloses a method for preventing the formation of adhesions following surgery or injury which is described as providing "crosslinked polymer compositions that include a first synthetic polymer containing multiple nucleophilic groups covalently bound to a second synthetic polymer containing multiple electrophilic groups. The first synthetic polymer is preferably a synthetic polypeptide or a polyethylene glycol that has been modified to contain multiple nucleophilic groups, such as primary amino (—NH.sub.2) or thiol (—SH) groups. The second synthetic polymer may be a hydrophilic or hydrophobic synthetic polymer, which contains or has been derivatized to contain, two or more electrophilic groups, such as succinimidyl groups. The compositions may further include other components, such as naturally occurring polysaccharides or proteins (such as glycosaminoglycans or collagen) and/or biologically active agents. Also disclosed are methods for using the crosslinked polymer compositions to effect adhesion between a first surface and a second surface; to effect tissue augmentation; to prevent the formation of surgical adhesions; and to coat a surface of a synthetic implant."

Related to surface coatings in general, U.S. Pat. No. 7,919,137 is directed to particularly to implantable or insertable medical devices which contain adherent polymeric layers and discloses medical "devices having adherent polymeric layers with depth-dependent properties" disclosing "a method of forming a medical device is provided, which includes: (a) contacting a substrate with a solution that contains (i) one or more types of polymers, (ii) a solvent that contains one or more types of solvent species, and (iii) one or more optional agents, for example, one or more therapeutic agents, among others; and (b) removing the solvent from the solution, thereby forming a polymeric layer on the substrate. The composition of the solution is changed over the course of forming the polymeric layer. In another aspect of the invention, a medical device is provided, which includes a substrate and a polymeric layer over the substrate. The polymeric layer contains a copolymer that contains differing first and second monomers. The lower surface of the polymeric layer contacting the substrate has a surface concentration of the first monomer relative to the second monomer that is higher than that of the upper surface of the polymeric layer opposite the substrate." The patent states that "Examples of medical devices benefiting from the present invention include implantable or insertable medical devices, for example, catheters (e.g., urological or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, embolization devices including cerebral aneurysm filler coils (including Guglilmi detachable coils and metal coils), embolic agents, hermetic sealants, septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia meshes, artificial ligaments, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other device that is implanted or inserted into the body." Similar disclosures are in related U.S. Pat. Nos. 7,914,807, 7,914,806, 7,901,726, 7,897,171, and 7,767,726.

U.S. Pat. No. 7,935,773 is directed to a device designed to close tissue openings and discloses "Water-swellable copolymers and articles and coatings made therefrom" in which describes that "compositions in accordance with this disclosure are water-swellable and can thus be used to close openings in tissue. The compositions include a copolymer containing repeating units of two or more monomers selected from the group consisting of 3-sulfopropyl acrylate potassium salt ("KSPA"), sodium acrylate ("NaA"), N-(tris (hydroxyl methyl)methyl)acrylamide ("tris acryl"), and 2-acrylamido-2-methyl-1-propane sulfonic acid (AMPS). The compositions can formed into a desired shape or may be used to coat at least a portion of a medical device, such as a hernia mesh, suture or surgical staple. After being dried, the copolymer will swell upon contact with moisture, such as blood or other bodily fluid." The reference also teaches that, optionally, therapeutically beneficial compounds may be incorporated into the present compositions, and, after application or implantation of the article or coated device, released there from.

These U.S. patents are incorporated herein by reference in their entirety. Not all of the above disclosures are directed to hernia prosthesis but do give technical background for general medical device construction and techniques to control tissue adhesion. Some of these earlier hernia repair prosthetics are complex. Although these medical advances in the field of hernia repair prosthetics are acknowledged for their usefulness and success in reducing the incidence of reoccurrence of the hernia, there remains a need for greater improvements in properly managing post operative adhesions in synthetic hernia mesh prosthesis and providing a solution that is cost effective to manufacture and implement.

Suture and Staple Background

Dermal wounds, whether from accidental injury, invasive medical procedures or cosmetic surgical modifications often result in some degree of scar formation. Scars can lead to adverse cosmoses, loss of functionality and can have significant adverse effects on a patient's quality of life. As such, wound healing and scar formation are highly researched areas and there is great potential to apply more recent findings toward innovative improvements to deliverable technologies. Thus a leading concern for all procedures in the wound care/elective surgery industry is a perfect cosmetic outcome with lack of visible scarring. Or substantial minimization of such scarring. Surgical practices have evolved considerably to minimize or hide scars from elective surgical procedures and various topical treatments have come to market which aim to reduce existing scars. Still, few products aim to actively inhibit scar formation at the extracellular level in the earliest stages of wound healing.

Fundamentally, scaring is the result of the body's rapid response to a wound, and a natural part of the healing process. Fibroblasts accumulate and proliferate in the wound site and hurriedly generate extracellular collagen matrix to strengthen the wound and allow for migration of cells.

In the suture, and to a lesser extent the surgical staple, fields the "coating" of these substrates with a variety of bioactive molecules is known, although most processes fail to immobilize the bioactive molecule and none of the prior art proposals appear to be demonstrably effective at promoting wound healing for minimizing scars, which almost none of these techniques have found commercial implementation.

U.S. Pat. No. 8,012,173 notes that so "far, only one polyglycolide-based thread material, marketed by Ethicon, which is coated with the antiseptic triclosan has been available on the market. This antiseptic is a chlorinated biphenyl derivative which has an antiseptic effect on gram-positive bacteria." The '173 patent itself teaches a surgical suture material with an antimicrobial surface with the surface exhibiting a coating containing a) at least one fatty acid, b) octenidine dichloride and/or dequalinium chloride and c) optionally oligomeric lactic acid esters. In addition, a process for coating surgical suture material is described which is characterized by the fact that the thread material is wetted with a homogeneous methanolic solution of octenidine dichloride and/or dequalinium chloride and subsequently the methanol is evaporated, a coating forming on the thread surface.

U.S. Pat. No. 7,837,708 discloses a suture which is combined intraoperatively with autogenous blood components. At least one strand of suture is placed into a sterile container and blood obtained from a patient is separated, using a centrifuge, for example, to retrieve certain healing components such as autogenous growth factors, to obtain an autogenous blood suspension. The autogenous blood suspension is added to the sterile container containing the strand of suture. The suture wicks up biologic components of the autogenous blood suspension to produce an enhanced suture. Surgical repairs using the enhanced suture are conducted by suturing a tear to itself or to bone, for example. Post-operatively, the biologic components leach from the suture to accelerate healing of the repair. Note also U.S. Pat. No. 2,493,943 essentially teaches catgut impregnated with human blood and U.S. Pat. No. 2,615,450 teaches the formation of hemoglobin containing sutures.

U.S. Patent Application Publication Number 2006-0286289 teaches an Intra-operative coating of sutures with therapeutic proteins, particularly growth factors such as rhGDF-5. including contacting a suture to a device containing a therapeutic agent.

U.S. Pat. No. 6,689,153 discloses a coated/impregnated anchoring device and/or suture to prevent infection, deliver site specific drugs, and deliver human growth factors to the surgical site. The coatings can include anti-microbial agents to prevent or fight infection en route to and at the surgical site. The coatings can also include site specific drugs and/or human growth factors to fight infection, anesthetize tissue and/or bone en route and at the site, promote tissue regeneration, promote bone regeneration, and/or other desired medical processes.

U.S. Pat. No. 6,878,757 discloses compositions with antimicrobial properties contain a fatty acid ester salt mixed with a bioabsorbable copolymer. These compositions are useful in forming coatings for surgical articles, including multifilament sutures. See also U.S. Pat. No. 7,829,133.

U.S. Pat. No. 5,716,376 discloses suture coatings made of a mixture of fatty acid esters, including calcium stearoyl lactylate, with a copolymer containing caprolactone. The coatings taught by this patent are used for absorbable sutures and other surgical articles and, in the case of sutures, impart improved properties to the suture, such as knot security, surgeon's throw, lubricity, knot run down, and/or knot repositioning.

It is known that suture materials are often coated with various substances to improve their handling characteristics. For example, U.S. Pat. Nos. 5,147,383, 5,123,912, 5,102,420, 5,100,433, 5,089,013, 4,844,067, 4,080,969, 4,043,344, 4,047,533, and 4,027,676 disclose coated surgical sutures with improved knot tie down properties.

U.S. Pat. No. 5,032,638 discloses a suture coating comprising a copolymer of poly (Beta-hydroxybutyrate) and a stearoyl lactylate containing alkaline-earth metals, and notes that calcium stearoyl lactylate and magnesium stearoyl lactylate can be added as lubricants.

U.S. Pat. No. 4,705,820 discloses a suture coating comprising a "random copolymer" and a lubricant, which can be a stearoyl lactylate.

U.S. Pat. No. 5,939,191 discloses a gut suture coated with a bioabsorbable copolymer obtained by polymerizing a major amount of epsilon-caprolactone and a minor amount of at least one other copolymerizable monomer in the presence of polyhydric alcohol as initiator.

U.S. Pat. No. 4,649,920 discloses a suture coated with an absorbable composition consisting essentially of a high molecular weight poly(alkylene oxide).

U.S. Pat. No. 3,896,814 discloses a collagen or catgut thread treated fatty compounds or derivatives of fatty compounds, such as glycerine, polyoxyalkylenes such as polyethylene glycol, or glycol derivatives.

These U.S. patents and U.S. Patent Application Publications are incorporated herein by reference in their entirety. The concept of providing a bioactive molecule on a suture or staple is well known and the above patents establish the amount of research in this effort and the lack of commercialization of such proposals evidence that such proposals have, to date, been ineffective at solving the stated problems in a cost effective manner. There remains a need in the art to provide a suture or staple with bioactive molecules to promote healing in a cost effective efficient manner.

SUMMARY OF THE INVENTION

One aspect of this invention is directed to an a polymeric synthetic suture with surface treatment to control tissue adhesion including a heparin surface treatment which provides heparin present in an amount to yield bioactivity of the heparin of at least one of i) an AT-III binding of at least 2 pmol/cm$^2$, and ii) a thrombin deactivation of at least 0.2 IU/cm$^2$.

ATIII references antithrombin III, also termed antithrombin, which is a small protein molecule that inactivates several enzymes of the coagulation system. The designations antithrombin I through to antithrombin IV originate in early studies carried out in the 1950s, with antithrombin I (AT-I) referencing to the absorption of thrombin onto fibrin after thrombin has activated fibrinogen. Antithrombin II (AT-II) refers to a cofactor in plasma, which together with heparin interferes with the interaction of thrombin and fribrogen. Antithrombin III (AT-III) refers to a substance in plasma that inactivates thrombin. Antithrombin IV (AT-IV) refers to an antithrombin that becomes activated during and shortly after blood coagulation. Only AT-III, and possibly AT-I are typically medically significant. AT-III is generally referred to solely as "Antithrombin." Heparin is measured in International Units (IU) instead of milligrams. One IU of heparin is defined as being the required amount of solution to prolong the clotting of 1 ml of whole blood for three minutes.

One aspect of the present invention is directed to a method of treating the surface of a surgical closure device with a biomolecule comprising the steps of: a) providing a polyolefin substrate forming a medical device; b) cleaning the polyolefin substrate; c) exposing the polyolefin substrate to a reactive gas containing acrylic acid and to plasma energy to yield a plasma-deposited polyacrylic acid coating on the polyolefin substrate; and d) attaching a biomolecule to the polyolefin substrate following formation of the plasma-deposited polyacrylic acid coating on the polyolefin substrate, and wherein the biomolecule is at least one of an antibacterial agent, antimicrobial agent, anticoagulant, heparin, antithrombotic agent, platelet agent, anti-inflammatory, enzyme, catalyst, hormone, growth factor, drug, vitamin, antibody, antigen, protein, nucleic acid, dye, a DNA segment, an RNA segment, protein, and peptide.

One aspect of the present invention is directed to a semi-continuous strip based production line for forming medical devices such as sutures staples and dental floss with surface treatment thereon to improve biologic performance.

It is noted that, as used in this specification and the appended claims, the singular forms "a," "an," and "the" include plural referents unless expressly and unequivocally limited to one referent. For the purposes of this specification, unless otherwise indicated, all numbers expressing quantities of ingredients, reaction conditions, and other parameters used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

All numerical ranges herein include all numerical values and ranges of all numerical values within the recited numerical ranges. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The various embodiments and examples of the present invention as presented herein are each understood to be non-limiting with respect to the scope of the invention. The features that characterize the present invention are pointed out with particularity in the claims which are part of this disclosure. These and other features of the invention, its operating advantages and the specific objects obtained by its use will be more fully understood from the following detailed description and the operating examples. These and other advantages are described in the brief description of the preferred embodiments in which like reference numeral represent like elements throughout.

BRIEF DESCRIPTION OF THE FIGURES

FIG. 1 is schematic representation of the methodology of surface treating synthetic hernia mesh substrates to control tissue adhesion in the hernia mesh prosthesis in accordance the present invention;

FIG. 2 schematically illustrates a synthetic hernia mesh prosthesis production line for surface treating one side of a synthetic hernia mesh prosthesis formed of polypropylene or polyester mesh with a collagen and heparin surface treatment in accordance with one embodiment of the present invention;

FIG. 3 schematically illustrates a synthetic hernia mesh prosthesis production line for surface treating one side of a synthetic hernia mesh prosthesis formed of polypropylene or polyester mesh with a collagen or heparin surface treatment in accordance with one embodiment of the present invention;

FIG. 4 schematically illustrates a synthetic hernia mesh prosthesis production line for surface treating one side of a synthetic hernia mesh prosthesis formed of polypropylene or polyester mesh with a siloxane surface treatment in accordance with one embodiment of the present invention;

FIG. 5 schematically illustrates a synthetic hernia mesh prosthesis production line for surface treating one side of a synthetic hernia mesh prosthesis formed of polypropylene or polyester mesh with a siloxane and heparin surface treatment in accordance with one embodiment of the present invention;

FIGS. 6A and B schematically illustrate a final synthetic hernia mesh prosthesis die cutting and sealing unit for use with the production lines of FIGS. 2-5 in accordance with one embodiment of the present invention;

FIGS. 7A and B schematically illustrate a preliminary synthetic hernia mesh prosthesis die cutting for use with the production lines of FIGS. 2-5 in accordance with one embodiment of the present invention;

FIG. 8 schematically illustrates the uniform collagen attachment in the synthetic hernia mesh prosthesis formed in the productions lines of FIG. 2 and one embodiment of FIG. 3;

DESCRIPTION OF THE PREFERRED EMBODIMENTS

Figure 9:
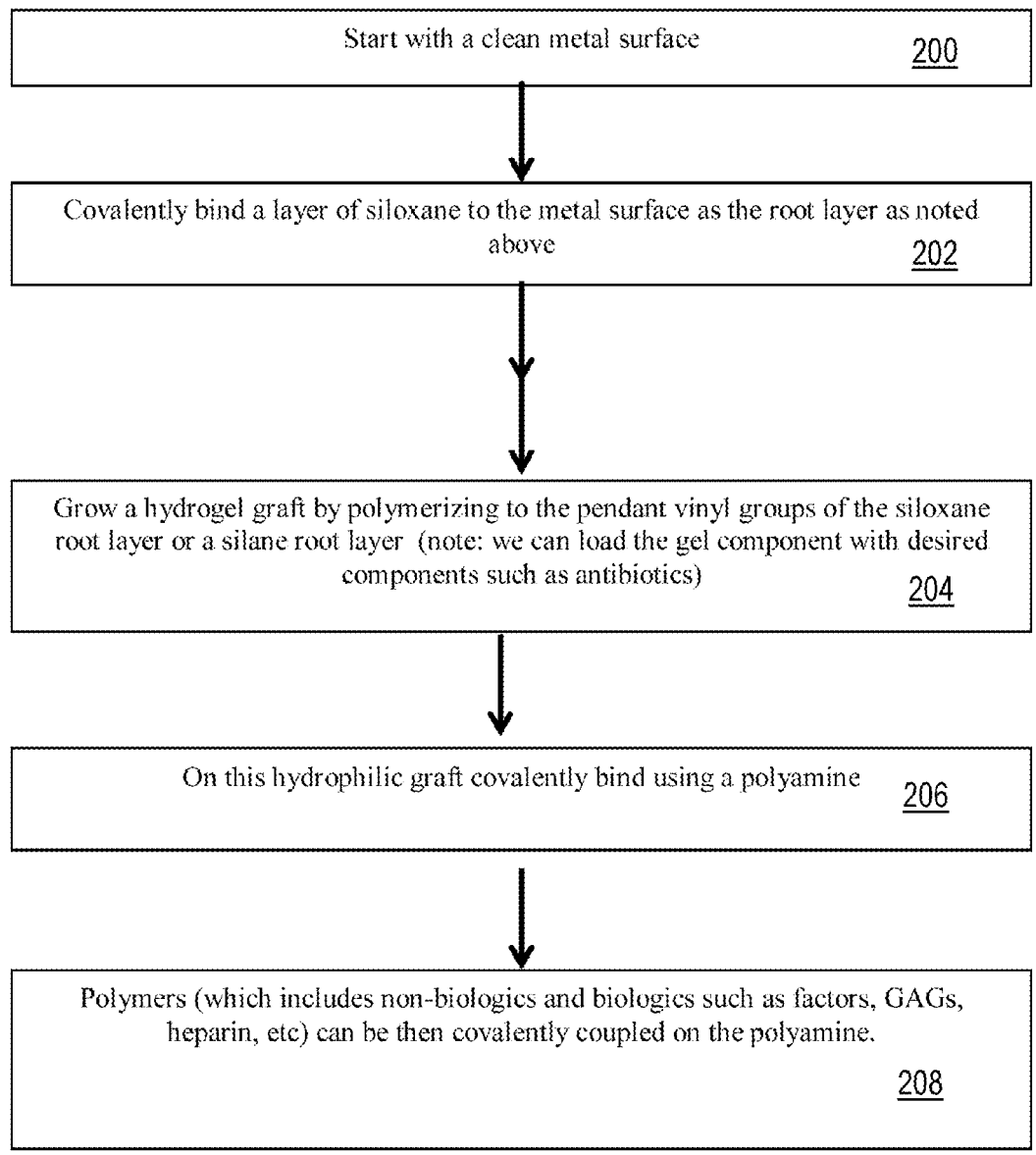
FIG. 9 is a schematic flow chart showing the steps of treating metal surgical fasteners in accordance with one aspect of the present invention.

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

All numerical ranges herein include all numerical values and ranges of all numerical values within the recited numerical ranges. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The various embodiments and examples of the present invention as presented herein are each understood to be non-limiting with respect to the scope of the invention.

As used in the following description and claims, the following terms have the indicated meanings:

The term "cure", "cured" or similar terms, as used in connection with a cured or curable composition, e.g., a "cured composition" of some specific description, means that at least a portion of the polymerizable and/or crosslinkable components that form the curable composition is at least partially polymerized and/or crosslinked. For example, the degree of crosslinking can range from 5% to 100% of complete crosslinking. In alternate embodiments, the degree of crosslinking can range from 35% to 85%, e.g., 50% to 85%, of full crosslinking. The degree of crosslinking can range between any combination of the previously stated values, inclusive of the recited values.

The term "curable", as used for example in connection with a curable film-forming composition (coating), means that the indicated composition is polymerizable or cross linkable, e.g., by means that include, but are not limited to, thermal, catalytic, electron beam, chemical free-radical initiation, and/or photoinitiation such as by exposure to ultraviolet light or other actinic radiation.

The terms "on", "appended to", "affixed to", "bonded to", "adhered to", or terms of like import means that the designated item, e.g., a coating, film or layer, is either directly connected to (superimposed on) the object surface, or indirectly connected to the object surface, e.g., through one or more other coatings, films or layers (superposed on).

The terms "attach", "couple", and "link" refer to securing a coating or biomolecule to a substrate, for example, by chemical covalent or ionic bonding, such that the coating or biomolecule is immobilized with respect to the substrate.

The term "rigid", as used for example in connection with a substrate, means that the specified item is self-supporting.

The phrase "an at least partial film" means an amount of film covering at least a portion, up to the complete surface of the substrate. As used herein, a "film" may be formed by a sheeting type of material or a coating type of material. For example, a film may be an at least partially cured polymeric sheet or an at least partially cured polymeric coating of the material indicated. The phrase "at least partially cured" means a material in which from some to all of the curable or cross-linkable components are cured, crosslinked and/or reacted.

The term "medical device" may be a device that has surfaces that contact tissue, blood, or other bodily fluids in the course of its operation, which fluids are subsequently introduced into patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like that are implanted in blood vessels or in the heart. This can also include temporary or permanent surgical closure devices such as sutures and staples. This can also include devices for temporary intravascular use such as catheters, guide wires, and the like which are placed into the blood vessels or the heart for purposes of monitoring or repair. As the substrate comes into contact with tissue in use, dental floss is included in this broad terminology of medical device.

The term "biomolecule" refers to a biologically active molecule.

A "biocompatible" material does not generally cause significant adverse reactions (e.g., toxic or antigenic responses) in the body, whether it degrades within the body, remains for extended periods of time, or is excreted whole. Ideally, a biocompatible material will not induce undesirable reactions in the body as a result of contact with bodily fluids or tissue, such as infection, coagulation, tissue death, tumor formation, allergic reaction, foreign body reaction (rejection) or inflammatory reaction.

A "blood compatible" material is one that will not induce undesirable reactions in the body as a result of contact with blood, such as blood clotting or infection. A blood compatible material is understood to be biocompatible.

General Medical Device

According to the present invention, processes are provided for preparing a substrate coated with a biomolecule. A typical process comprises:
a) providing a substrate;
b) coating the substrate with a polysiloxane or acrylamide;
c) rendering the polysiloxane and/or acrylamide surface amino functional; and
d) contacting the amino-functional polysiloxane surface with a biomolecule under conditions effective to attach the biomolecule to the substrate.

The surface of the resulting coated substrate is biocompatible and preferably blood compatible. In particular, the resulting coated substrate is permeable to oxygen and carbon dioxide and remains so during exposure to bodily fluids by preventing adhesion of phospholipids.

Substrates suitable for use in the process of the present invention include metals, polymers, ceramic and glass. They are substantially insoluble in body fluids and are generally designed and constructed to be placed in or onto the body or to contact fluid of the body, most often blood. The substrates have the physical properties such as strength, elasticity, permeability and flexibility required to function for their intended purpose, and are typically rigid, i.e., capable of maintaining their shape and supporting any subsequently-applied coatings or films. The substrates can be purified, fabricated and sterilized easily; will substantially maintain their physical properties and function during the time that they remain implanted in or in contact with the body or bodily fluid. Examples of such substrates include: metals such as titanium/titanium alloys, TiNi (shape memory/super elastic), aluminum oxide, platinum/platinum alloys, stainless steels, and other metal alloys known to be useful for medical devices, pyrolytic carbon, silver or glassy carbon; polymers such as polyurethanes, polycarbonates, silicone elastomers, polyolefins including polyethylenes or polypropylenes (such as found in hernia mesh substrates and suture materials discussed further below), polyvinyl chlorides, polyethers, polyesters, nylons, polyvinyl pyrrolidones, polyacrylates and polymethacrylates such as polymethylmethacrylate (PMMA), n-Butyl cyanoacrylate, polyvinyl alcohols, polyisoprenes, rubber, cellulosics, polyvinylidene fluoride (PVDF), polytetrafluoroethylene, ethylene tetrafluoroethylene copolymer (ETFE), acrylonitrile butadiene ethylene, polyamide, polyimide, styrene acrylonitrile, and the like; minerals or ceramics such as hydroxapatite; human or animal protein or tissue such as bone, skin, teeth, collagen, laminin, elastin or fibrin; organic materials such as wood, cellulose, or compressed carbon; and other materials such as glass, or the like.

The substrate used in the process of the present invention often comprises a surface of a medical device. Substrates which may be coated with biomolecules in accordance with the present invention include, but are not limited to, those to be used in the manufacture of medical devices such as surgical implants, prostheses (such as hernia mesh discussed further below), and any artificial part or device which replaces or augments a part of a living body or comes into contact with bodily fluids, particularly blood. The substrates can be in any shape or form including tubular, sheet, rod and articles of shapes required for particular uses. Such shaped substrates are typically coated using the process of the present invention prior to manufacture of the medical device in which they are used. Various medical devices and equipment usable in accordance with the invention are known in the art. Examples of devices include catheters, hernia mesh, suture material, tubing, and fiber membranes. Examples of catheters include central venous catheters, thoracic drain catheters, and angioplasty balloon catheters. Examples of tubing include tubing used in extracorporeal circuitry, such as whole blood oxygenators. Examples of membranes include polycarbonate membranes, haemodialysis membranes, and membranes used in diagnostic or biosensor devices. Also included are devices used in diagnosis, as well as polyester yarn suture material such as polyethylene ribbon, and polypropylene hollow fiber membranes. Further illustrations of medical devices include autotransfusion devices, blood filters, blood pumps, blood temperature monitors, bone growth stimulators, breathing circuit connectors, bulldog clamps, cannulae, grafts, implantible pumps, impotence and incontinence implants, intra-ocular lenses, leads, lead adapters, lead connectors, nasal buttons, orbital implants, cardiac insulation pads, cardiac jackets, clips, covers, dilators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, batteries, bone cement, breast implants, cardiac materials, such as fabrics, felts, mesh, patches, cement spacers, cochlear implant, defibrillators, generators, orthopedic implants, pacemakers, patellar buttons, penile implants, pledgets, plugs, ports, prosthetic heart valves, sheeting, shunts, umbilical tape, valved conduits, and vascular access devices. Hernia mesh and surgical closure members, namely sutures and surgical staples, are also included and are discussed separately below.

The method of the present invention also is particularly applicable to blood gas exchange devices, e.g., oxygenators. This includes both sheet and tubular forms of membrane oxygenators, which are well known in the art. In a membrane oxygenator, the blood is separated from direct contact with the oxygenating gas by a membrane, which is disposed within a hollow housing. This membrane is microporous or semipermeable, that is, capable of permitting carbon dioxide and oxygen to permeate through it while at the same time preventing the blood itself from passing therethrough.

There currently are two types of membrane oxygenators. One type is referred to as a hollow fiber oxygenator, and is illustrated in U.S. Pat. No. 4,239,729. A hollow fiber oxygenator employs a large plurality (typically thousands) of microporous or semipermeable hollow fibers disposed within a housing. These hollow fibers are sealed in the end walls of the housing; the end walls are then fitted with skirted end caps. One end cap is fitted with an inlet, and the other is fitted with an outlet. In the Hasegawa et al. oxygenator, the hollow fibers are aligned in the housing so that their longitudinal axes are generally parallel to the longitudinal axis of the housing. In this device, blood enters through the inlet of one end cap, passes through the lumens of the hollow fibers, and exits through the outlet of the other end cap. Oxygenated gas enters the device through the inlet in the peripheral wall near one end of the device, passes over the outer surfaces of the hollow fibers, and exits the device through the outlet in the peripheral wall near the other end of the device. It will be understood that carbon dioxide diffuses from the blood flowing inside the hollow fibers through the fiber walls into the stream of oxygenating gas. At the same time, oxygen from the oxygenating gas flowing over the outer surfaces of the hollow fibers diffuses through the walls of the hollow fibers into the lumens thereof to oxygenate the blood flowing therethrough.

Since the development of this type of oxygenator, other oxygenators comprising hollow fibers have been developed. These oxygenators typically comprise a plurality of hollow fibers disposed within a hollow housing and arranged so that blood typically flows over the hollow fibers and gases typically flow through the hollow fibers. Many configurations are possible as to the direction of fluid flow and the arrangement of fibers. The fibers may be in a linear, circular, or spiral arrangement, for example, or may be wrapped or wound around a core in various configurations. Hollow fiber membrane oxygenators are described, for example, in U.S. Pat. No. 4,975,247 and U.S. Pat. No. 5,395,468. In certain embodiments of the present invention, the substrate being coated comprises hollow fibers that are to be used in the manufacture of a blood oxygenator.

A second type of membrane oxygenator, called the flat plate membrane oxygenator, employs one or more thin, flat sheets of microporous membrane. In its most basic form, the flat plate oxygenator has a single sheet of microporous membrane sealed into a housing so as to provide in the housing a first compartment (the "blood compartment") for the flow of blood, and a second compartment (the "gas compartment") for the flow of an oxygenating gas. Each of the compartments is fitted with an inlet and an outlet. Blood flows into and out of the blood compartment and the oxygenating gas flows into and out of the gas compartment. Oxygen passes from the oxygenating gas across the membrane into the blood flowing through the blood compartment. Carbon dioxide passes from the entering blood across the membrane to be entrained in the oxygenating gas. The exiting blood, now reduced in carbon dioxide and enriched in oxygen, is returned to the patient.

In certain embodiments of the present invention, the process may include a step of cleaning the substrate prior to step b) of the process, to remove any surface contaminants or impurities. Such cleaning may be done, for example, by placing the substrate in a plasma chamber, infusing air, oxygen, and/or nitrogen into the plasma chamber, and then exposing the device to plasma energy. Air and oxygen plasma treatments introduce oxygen containing functionalities on the surface of polymeric substrates. For example, hydroxyl, carboxyl, and other oxygen containing functionalities are introduced on the surface of polyethylene. As a result, the surface becomes more polar and wettability increases. Low molecular weight contaminants are effectively removed by the combined effect of plasma and vacuum. Air plasma treatment of metallic substrate materials mostly provides a cleaning effect, removing hydrocarbons and other organic contaminants from the metal surface. Plasma treatment for cleaning purposes may be conducted in the same manner as reactive gas treatment, discussed below.

In step b) of the process of the present invention, the substrate is coated with a polysiloxane. This coating step may be accomplished in any of several manners. It is possible to contact the substrate with a polysiloxane in a liquid carrier. Contact may be by brushing, dipping (immersion), flow coating, spraying and the like. Immersion may include stirring or other agitation of the coating composition, by use of a stirring device or by movement of the substrate to be coated through the composition. More often, however, the substrate is exposed to a reactive gas containing siloxane functional groups and plasma energy to yield a plasma-deposited polysiloxane surface on the substrate. Such plasma treatments typically take place within a plasma chamber containing electrodes, across which a voltage is applied, as known in the art. A stream of gas is fed into the chamber. Gases may vary and include, for example, hexamethyldisiloxane and/or tetramethyldisiloxane. When a high frequency voltage is applied between the electrodes, current flows into the chamber, forming a plasma, which is a glowing electrical discharge within the gas. Reactive chemical species are formed in this electrical discharge.

The plasma-deposited surface comprises a polymeric layer deposited onto the substrate. Siloxane molecules are fragmented in the plasma phase and recombine to yield a high molecular weight polymeric compound that deposits as a film on the device surface. The structure of the deposited film depends on the stream gas chemistry and the treatment conditions. Films deposited by this plasma process are, typically, highly cross-linked, pin-hole free, homogeneous, and show good adhesion to the device. Following cessation of the high frequency voltage applied between the electrodes, the gas stream flow may be continued in the chamber in order to quench the substrate.

Step c) of the process of the present invention comprises rendering the polysiloxane surface amino functional. In certain embodiments of the present invention, step c) comprises contacting the polysiloxane surface with an amino- and/or imino-functional compound for a time sufficient to effect adsorption of the amino- and/or imino-functional compound onto the polysiloxane surface. In such embodiments, the amino- and/or imino-functional compound may comprise polyethyleneimine, an amino-functional silane and/or diaminopropane. Examples of suitable amino functional silanes include amino-functional silanes sold as the Dow Corning Z-silane series. Depending on the identity of the compound, it may be present in a liquid carrier, particularly when the compound is an amino-functional silane. Again, contact may be by brushing, dipping (immersion), flow coating, spraying and the like, but is typically by immersion. After adsorption of the compound onto the surface, any imino-functional groups may be reduced to amino-functional groups by addition of a suitable reducing agent to the liquid carrier.

Alternatively, step c) may comprise exposing the plasma-deposited polysiloxane surface to ammonia or an organic amino-functional gas and to plasma energy to yield an amino-functional plasma-deposited surface. Suitable organic amino-functional gases include amino-functional polysiloxane, diaminopropane, and allyl amine.

Prior to attachment of the biomolecule to the amino-functional polysiloxane surface in step d), it may be desirable to expose the amino-functional polysiloxane surface to a reactive gas containing acrylic acid and to plasma energy to yield a plasma-deposited polyacrylic acid, or acrylamide, coating on the surface, which may be considered a hydrogel surface. This step is particularly useful when the polysiloxane has been applied using plasma energy, and is suitable for the preparation of medical devices that do not facilitate mass transfer such as gas exchange. The plasma deposited acrylamide surface can also be utilized in place of the polysiloxane surface and the acrylic layer can be made amino-functional.

In step d) of the process of the present invention, the amino-functional polysiloxane surface (and/or acrylic surface) is contacted with a biomolecule under conditions effective to attach the biomolecule to the substrate. Examples of biomolecules that may be attached to the surface include antibacterial agents, antimicrobial agents, anticoagulants, antithrombotic agents, platelet agents, anti-inflammatories, enzymes, catalysts, hormones, growth factors, drugs, vitamins, antibodies, antigens, nucleic acids, dyes, a DNA segment, an RNA segment, protein, and peptides. Often, when the medical device to be coated is designed to come in contact with blood, in particular when the medical device is a blood oxygenator, the biomolecule comprises heparin.

Attachment of the biomolecule to the amino-functional polysiloxane surface can be accomplished by any of a number of methods known to those skilled in the art. One particularly preferred method is an oxidation method involving the use of periodate. The biomolecule, usually heparin, is contacted with a periodate in a buffered aqueous solution and allowed to react. This controlled oxidation provides a limited number of reactive aldehyde groups per molecule. The periodate is a water-soluble periodate, preferably, an alkali metal periodate, such as sodium periodate. When the biomolecule is heparin, the amount of periodate used is sufficient to react with no more than two of the sugar units in the heparin molecule (i.e., the basic disaccharide residues constituting the structure of the glycosaminoglycan). If the periodate used is sodium periodate and the heparin used is a commercially available injectable form of heparin (e.g., its sodium salt with activity of 160 units/milligram), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to about 8 can be used. A lower pH (e.g., an acetate buffer at pH 4.5) is preferred if a rapid reaction is desired while a more neutral pH (e.g., a phosphate buffer at pH 6.88) is preferred for a slower reaction with a longer storage life. With the acetate buffer at a pH of 4.5, the reaction should proceed for about 3 hours, while with a phosphate buffer at a pH or 6.88, the reaction should proceed for about 16 hours. If desired, the reacted mixture may then be stored prior to use at about 5° C.

The reacted mixture is diluted and the pH adjusted in order to bring the pH of the mixture to a pH that is favorable for the coupling reaction between the biomolecule and the amino-functional polysiloxane. A mild reducing agent, such as sodium cyanoborohydride, is added to the diluted mixture to effect the reduction of the bonds formed between the reactive aldehyde groups on the oxidized biomolecule and the amine functional groups on the polysiloxane coated on the substrate surface. The substrate surface being treated is then contacted with (e.g., immersed in or flushed with) the diluted mixture at a sufficient temperature and for a sufficient time to complete the reaction (i.e., attach the biomolecule). This time can range from about 30 seconds to about 2 hours at temperatures ranging from about 20° C. to about 60° C. For example, at room temperature (i.e., about 20° C. to about 25° C.), the substrate coated with the amino-functional polydimethylsiloxane can be flushed with a solution of a biomolecule over a period of 30 seconds to 5 minutes for effective biomolecule attachment.

Substrates coated with biomolecules according to the process of the present invention are biocompatible, and are typically blood compatible, while remaining permeable to gases including oxygen and carbon dioxide.

The present invention is more particularly described in the following examples, which are intended to be illustrative only, since numerous modifications and variations therein will be apparent to those skilled in the art. Unless otherwise specified, all parts and percentages are by weight.

EXAMPLES

One group of modified bulk material was prepared, a total of 34 hollow fiber strips underwent a 40 sec $O_2/N_2$ plasma cleaning followed by a 40-second siloxane deposition. Within 48 to 72 hours the siloxane treated material was heparinized. (NH)

Materials and Methods
1. Microporous Hollow Fiber Membrane Bulk Material Lot #13502-4-4 precut to 36" lengths
2. Glass microscope slide
3. Siloxane-Tetramethyldisiloxane, 97% P/N 235733//Batch 04526KC (Aldrich)
4. For chemical list see table IV Set-Up and Pre-Testing
1. Glass microscope slide
2. After placing the glass slide in the reactor and pulling vacuum to <100 mtorr, oxygen was allowed through the mass flow controller (MFC1) at a rate of 20% and $N_2$ through MFC2 at a rate of 80% of total flow, and the pressure control was set to 250 motor. Plasma power was set for 200 W (power). See table I below Pre-Test for Uniformity of Siloxane Deposition on Glass Slide

TABLE I

| | | Set-Up Parameters | | | | | |
|---|---|---|---|---|---|---|---|
| Material Description | Process Description | Pressure (mtorr) | MFC1/MFC2 | Set Power Watts | Time Seconds | Siloxane Temperature Set Point | Comments |
| Glass microscope slide and PP HF | 20% $O_2$ 80% $N_2$ Clean | 250 | 0.2/.8 | 200 | 40 | NA | Contact angle 0 - wet out |
| | Siloxane Deposition | 250 | NA | 200 | 40 | NA | Contact angle >90 - non wet |

Set-Up Procedure

Siloxane vapors from a feed chamber were introduced through a ball valve that communicated with the plasma reactor. Vacuum was pulled to <100 mtorr before opening the ball valve. The valve was opened to control pressure at 250 mtorr from the siloxane vapor.

Results from first test for uniform coverage in the reactor showed that the glass slide made the conversion from hydrophilic to hydrophobic.

Siloxane Deposition of Bulk Material
1. Two 36" hollow fiber strips per/run were placed on the reactor tray and carefully taped underneath. See diagram below
2. $O_2//N_2$ cleaned for 40 seconds
3. Siloxane deposition 40 seconds
4. Contact angle was performed on a glass microscope slide after each siloxane treatment/run.
5. For storage and transporting after siloxane deposition, the strips were placed between lint-free towels.

TABLE II

| | | Set-Up Parameters | | | | | | |
|---|---|---|---|---|---|---|---|---|
| Material Description | Process Description | Run Number | Pressure (mtorr) | MFC1/MFC2 | Set Power Wattts | Time Seconds | Siloxane Temperature Set Point | Contact Angle Glass Slide |
| (2) 36 × 4" Strips | $O_2//N_2$ Clean | 1 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 2 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 3 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 4 | 250 | 0.2 | 200 | 40 | NA | 0 - wet out |
| (1) Glass Slide | Siloxane | | | 0.8 | | 40 | | >90 - non wet |

TABLE II-continued

| | | | | | Set-Up Parameters | | | |
|---|---|---|---|---|---|---|---|---|
| Material Description | Process Description | Run Number | Pressure (mtorr) | MFC1/ MFC2 | Set Power Wattts | Time Seconds | Siloxane Temperature Set Point | Contact Angle Glass Slide |
| (2) 36 × 4" Strips | O$_2$//N$_2$ Clean | 5 | 250 | 0.2 | 200 | 40 | NA | 0 - wet out |
| (1) Glass Slide | Siloxane | | | 0.8 | | 40 | | >90 - non wet |
| (2) 36 × 4" Strips | O$_2$//N$_2$ Clean | 6 | 250 | 0.2 | 200 | 40 | NA | 0 - wet out |
| (1) Glass Slide | Siloxane | | | 0.8 | | 40 | | >90 - non wet |
| (2) 36 × 4" Strips | O$_2$//N$_2$ Clean | 7 | 250 | 0.2 | 200 | 40 | NA | 0 - wet out |
| (1) Glass Slide | Siloxane | | | 0.8 | | 40 | | >90 - non wet |
| (2) 36 × 4" Strips | O$_2$//N$_2$ Clean | 8 | 250 | 0.2 | 200 | 40 | NA | 0 - wet out |
| (1) Glass Slide | Siloxane | | | 0.8 | | 40 | | >90 - non wet |

Wet Chemistries (PEI and Heparin)

34 siloxane treated bulk material sheets (pre-cut to ~17×4") then carefully layered into (2) vessels and modified as follows.

Step One—Polyethyleneimine (PEI) Amination:

Preparation of BASF PEI solution [0.1%]: Total=1800 g
1764 g 0.1M Borate Buffer pH 9.0
36 ml of a 5% BASF PEI stock solution PEI and borate buffer were combined a glass beaker and allowed to stir for 15 minutes, the PEI solution was dispensed into (2) 2000 ml rectangle vessels each containing 16 (17×4") layered material strips. The container's were covered and placed on an orbital shaker and allowed to agitate @90 rpm for 75 minutes @ ambient temperature. After PEI adsorption, the aminated material was rinsed several times with DI H$_2$O. After rinsing a small sample was removed, stained with Ponceau S and evaluated for uniformity.

Ponceau S Staining Results:

The aminated sample showed a light uniform pink stain, indicating uniform coverage of PEI.

Step Two—Heparinization:

Preparation of Deaminated Heparin (DH) solution Total=1800 g
1.8 g DH heparin=[1 mg/ml]
1800 g 0.5M NaCl adjust to pH 4.0
0.18 g NaCNBH$_3$=[0.1 mg/ml]

Heparin was dissolved in the pre-mixed NaCl solution, then adjusted to pH 4.0±0.1, the solution was then preheated to 55° C. After the solution reached temperature the NaB-HCN$_3$ was added and allowed to mix for 5-10 minutes. The preheated heparin solution was dispensed into (2) 2000 ml rectangle vessel containing the aminated material, the container's were covered and placed in a pre-heated 55° C. Orbital shaker @ 90 rpm for 2 hours 55° C. After heparinization the modified material was rinsed with DI H$_2$O, 1M NaCl, followed with a final DI rinse. After rinsing a small section was removed, stained with Toluidine Blue and evaluated for uniformity.

Toluidine Blue O Staining Results:

Visual observations showed the heparinized sample to have a light but uniform purple stain, indicating uniform coverage of heparin.

Hernia Repair Prosthetic

FIG. 1 is schematic plan view of schematic representation of the methodology of surface treating polymeric synthetic hernia mesh substrates to improve healing and to control tissue adhesion in the hernia mesh prosthesis in accordance the present invention. Preferably the synthetic hernia mesh substrates are formed from one or more synthetic hernia mesh layers formed of monofilament polypropylene, monofilament polyester, multi-filament polypropylene and multi-filament polyester mesh layers. Monofilament polypropylene mesh is likely the most common synthetic hernia repair mesh used today.

The present invention can utilize a wide variety of known monofilament polypropylene mesh particularly one mesh layer or two or more mesh layers can be combined to form the prosthesis of the present invention. However each monofilament polypropylene mesh of the present invention will preferably be formed of polypropylene monofilaments having a diameter of about 0.03 mm to about 0.3 mm in diameter, typically about 0.05 mm to about 0.25 mm in diameter, and more preferably about 0.08 mm to about 0.20 mm in diameter. Each monofilament polyester mesh of the present invention will preferably be formed of polyester monofilaments having a diameter of about 0.02 mm to about 0.35 mm in diameter, typically about 0.05 mm to about 0.25 mm in diameter, and more preferably about 0.08 mm to about 0.20 mm in diameter.

Pore size is also an important characteristic of defining hernia repair mesh with some studies reviewing the efficacy of "large pore size" vs "small pore size" although what qualifies as large and small vary between studies. Pore size is rated differently as some choose to identify an average pore diameter, while others tend to identify a pore length and width opening size. Pore area seems a more applicable standard for rating mesh pore size in hernia mesh. However, each polypropylene mesh of the prosthesis of the present invention will preferably be formed having a typical average pore size between about 0.4 mm$^2$ to about 10 mm$^2$. Each polyester mesh of the prosthesis of the present invention will preferably be formed having a typical average pore size between about 0.2 mm$^2$ to about 7 mm$^2$.

Mesh weight, defined in grams/meter$^2$ or oz/yard, is also an important characteristic of defining hernia repair mesh with some studies reviewing the efficacy of "lightweight mesh" vs "heavy mesh" although what qualifies as lightweight and non-lightweight is less uniform throughout the studies. The relevant parameter for weight is the total prosthesis weight, wherein the polypropylene mesh prosthesis of the present invention will typically be formed having a weight between about 15 to 150 grams/meter$^2$, more preferably about 25 to 100 grams/meter$^2$. The polyester mesh prosthesis of the present invention will typically be formed having a weight between about 15 to 200 grams/meter$^2$, more preferably about 30 to 120 grams/meter$^2$.

Overall thickness of the prosthesis represents another important criterion for hernia mesh. The relevant parameter for thickness is the total prosthesis thickness, wherein the polypropylene prosthesis of the present invention will typically be formed having a thickness between about 0.25 to 2.5 mm, more preferably about 0.3 to 1.5 mm, and even more preferably 0.5 to 1.3 mm. The polyester prosthesis of the present invention will typically be formed having a thickness between about 0.20 to 1.8 mm, more preferably about 0.3 to 1.5 mm, and even more preferably 0.5 to 1.3 mm.

Finally, the strength of the mesh is highly important for making sure the mesh can perform its primary function of preventing a reoccurrence of the hernia. Strength of the mesh is typically identified as burst strength, measured in kPa or psi, and break strength, measured in N/2.5 cm or lbs/in. These parameters are given for individual mesh layers of the prosthesis of the invention wherein each polypropylene mesh layer of the prosthesis of the invention typically displays burst strength of about 40 to 180 psi and break strength (MD) of about 20 to 130 lbs/in (MD). Each polyester mesh layer of the prosthesis of the invention typically displays burst strength of about 20 to 175 psi and break strength (MD) of about 7.5 to 130 lbs/in (MD).

At least one substrate or mesh layer 10 forming the polymeric synthetic hernia repair prosthesis of the present invention will include a surface treatment on at least one tissue-facing surface of the prosthesis to control tissue adherence in the prosthesis. The substrate 10 which includes a surface treatment on at least one tissue-facing surface of thereof to control tissue adherence, or other desired mesh properties, in the prosthesis will undergo a surface activation or actuation step 12 to prepare the substrate or mesh layer 10 for intermediate chemistry or chemistries step 14 that allow the mesh layer 10 to receive the desired surface treatment in the form of the desired biomolecule at step 16, typically heparin or collagen as set forth in detail below.

FIG. 2 schematically illustrates a synthetic hernia mesh prosthesis production line for surface treating one side of a polymeric synthetic hernia mesh prosthesis formed of polypropylene or polyester mesh with a collagen and heparin surface treatment in accordance with one embodiment of the present invention. The substrate or mesh layer 10 is preferably in the form of a flexible strip or roll as shown, allowing for manufacturing in a semi-continuous process as illustrated. As discussed below a pair of mesh layers form the two layer polymeric synthetic hernia mesh prosthesis 130 of FIG. 2 and thus each layer 10 may be a "lightweight" mesh. For example such as a polypropylene mesh known as model number PPKM301 from Surgicalmesh which has 0.08 mm diameter monofilament mesh polypropylene having 1.5×1.2 mm typical pore size (1.8 mm$^2$), and about 25 GSM density (grams/meter$^2$), Burst strength is 295 kPa (43 psi), Break Strength of 99 N/2.5 cm (22 lbs/in) MD and 114 N/2.5 cm (26 lbs/in) CMD, Break Elongation of 62% MD and 92% CMD and a thickness of 0.31 mm. Similar lightweight polyester meshes may also be used for a two layer polyester multilayer mesh 130 of FIG. 2, such as forming the layers 10 from polyester mesh known as model number PETKM3002 from Surgicalmesh which has 1.0×0.9 mm typical pore size (0.9 mm$^2$), and about 30 GSM density (grams/meter$^2$), Burst strength is 269 kPa (39 psi), Break Strength of 110 N/2.5 cm (25 lbs/in) MD, Break Elongation of 54% MD and 95% CMD and a thickness of 0.23 mm.

The initial process is mesh cleaning at cleaning station 20, which is important mainly because most polymeric materials, such as polypropylene or polyester mesh layers 10, have processing aids or contaminants that are left on the surface, and these lead to poor adhesion of subsequent chemistries or surface modifications. The cleaning step at station 20 is schematically shown as a strip-roll 10 semi-continuous process for illustrating a preferential manufacturing arrangement wherein the strip of material is weaved through the cleaning station 20 along tensioner rolls 22. The vast majority of the left over contaminants are removable by isopropyl alcohol cleaning which can be supplied onto the strip via nozzles 24 followed by drying rolls 26. The cleaning process at station 20 as shown is a two stage process allowing for a more thorough cleaning of the mesh layer 10 and also allowing for the formulation of the cleaning solution to be varied as desired for each stage to improve cleaning results. Attempting to perform a plasma treatment before removing the contaminants on the substrate or layer 10 can result in modification of these contaminants versus modification of the polypropylene or polyester base material.

An alternative two step cleaning process for station 20 would be an ultrasonic cleaning in isopropyl alcohol followed by some drying step and protection (covering in station 20 to prevent dust or chemisorption) from airborne contamination. The cleaned strip 30 is rolled onto a roll or mandrel which may be driven or powered and will typically be used to pull the strip 10 through the cleaning station 20 along the tensioner rolls 20 through the nozzles 24 and drying rolls 26.

As a further possible alternative for cleaning station 20 one may perform a plasma cleaning step which is usually accomplished by an oxygen plasma, or a clean dry air (mixture of Nitrogen and oxygen) gas that is less aggressive. This will ablate the contaminants from the surface of the strip 10. Water and surfactant cleaning processes possibly may be used as a further alternative, but the removal of surfactants becomes highly critical and thus this cleaning process is less optimal.

Following the cleaning station 10 the cleaned polypropylene or polyester mesh roll or layer 30 is moved to the activation step 12 of the plasma treatment in plasma chamber 40 prior to intermediate chemistries step 14. For polypropylene mesh 30, the preferred approach is a plasma deposited layer of propene from supply 52 as this has shown optimal for free radical grafting in the intermediate chemistries step 14. Substantially similar plasma deposition would work for polyester mesh 30. The particulars of this type of plasma deposition can be found in U.S. Pat. No. 6,632,470, which is incorporated herein by reference.

The plasma deposition in chamber 40 on layer 30 is schematically shown as a semi-continuous process for illustrating a preferential manufacturing arrangement wherein the strip of material 30 is weaved through the plasma chamber 40 along tensioner rolls 42 between ground electrode 44 and active electrode 46. The chamber 30 includes a power supply 48 for the electrodes 46 and 44 and a vacuum 50.

It is preferable to use active electrode 46 and ground electrode 44 within the reactor chamber 40 as opposed to the chamber wall being the ground. The spacing between the active electrode 46 and the ground electrode 44 will be about 2 inches, and the power from supply 48 will be between about 40 and 100 Watts, and the pressure of vacuum 50 will be about 120 mTorr. These conditions vary reasonably from reactor to reactor.

The activated strip or layer 60 is rolled onto roll or mandrel which is powered and will typically be used to pull the strip 30 from the feed reel through the plasma chamber 40 along the tensioner rolls 42 through the electrodes 44 and 46 and the resulting activated layer 60 onto the mandrel. The provision of the take up reel or mandrel and the feed reel within the plasma chamber 40 for feeding the mesh through as shown allows for semi-continuous production system and allows for effective scaled up of production with reasonable plasma chamber 40 sizes.

Alternatively for polypropylene mesh 30, an ozone treatment can be utilized instead of plasma activation. Also irradiation with beta (electron beam) is commercially viable as an alternative activation method. Polyester (PET) mesh layer will limit preferred options to a plasma deposited layer of propene followed by grafting as PET under irradiation, or ablative plasma treatment, yields surfaces that have residual low molecular weight fragments that are not optimal for coating processes.

Following the activation step 12 in the plasma chamber is the intermediate chemistry represented by a radical graft 74 in chamber 70 in which the strip or layer of activated mesh 60 is weaved over tensioning rolls 62 and rolls 72 associated with chamber 70 and into the radical graft substance within chamber 70. Chamber 70 will graft an acrylic surface treatment or layer (47 in FIG. 8) onto the surface of the activated mesh 60. The grafted acrylic layer 47 may be formed as copolymerized acrylamide and acrylic acid monomers in a copolymer form, or alternatively homopolymers of polyacrylamide or polyacrylic acid, which forms a hydrogel surface. The thickness of the graft layer 47 on the substrate or layer 60 should not exceed 1-2 microns. At levels thicker than this and the grafted layer is susceptible to mechanical abrasion forces in handling. The cleaned activated surface of layer 60 allows for a necessary high level of uniformity of the grafted layer 47 as can be demonstrated by a stain showing uniform coverage, and ultimately a XPS surface analysis showing signature grafted elemental and functional group analysis.

It is possible, as an alternative to the radical grafting step here to directly plasma deposit a layer of polyacrylic acid. The possible draw back with such an alternative is that the polyacrylic surface from plasma deposition would not have the same thickness as grafting and not couple sufficient amounts of collagen and/or heparin. However directly plasma deposit a layer of polyacrylic acid and eliminating the radical graft step alternative is believed to be a viable alternative process.

Following the radical grafting of the acrylic surface treatment onto the treated or activated mesh layer 60, the strip or layer 60 and associated grafted surface treatment is directed to a hydrolysis chamber 80 with liquid bath submersion of the layer 60 via tensioner rolls 82 into a hydrolyzing solution 84. The hydrolyzing solution is: 0.5M NaHCO3 and 0.356M NaOH at pH 10.1 and is used to treat the grafted material and strip 60 for about 15-60 minutes at about 50 degrees centrigrade. The hydrolysis cleans up any loose excessive grafted material. Additionally when utilizing a relatively high percent polyacrylic acid content then this step will neutralize the free acid carboxylic groups with a sodium counter ion for optimal subsequent chemistries.

The hydrolyzing step above could be replaced with a simple deionized water rinse, but the hydrolysis described performs better at addressing loose grafted material and optimizing subsequent chemistries.

Following the hydrolysis treatment in chamber 80 the strip 60 and associated acrylic surface treatment is directed to a station or chamber 90 for collagen 94 application, also called collagen immobilization, using tensioning or tensioner rolls 92.

The chamber 90 is only schematically representative of the process which will actually be divided into a series of sections or steps. The following is a more detailed and precise description of an acceptable process for coupling collagen to a polyacrylic acid surface. Initially the surface grafted layer 60 is immersed in a 0.1 M di-sodium tartrate dehydrate buffer solution adjusted to pH of 3.0 (by selective addition of 1 NHCL) for four hours at ambient or room temperature. The strip 60 is then sent through a triple rinse of deionized water and subsequently immersed in a 0.02 M MES buffered solution adjusted to a pH of 4.0-4.5 and further containing 0.01 M EDC and 0.01 M NHS dissolved therein, for an carbodiimide activation reaction that continues for about 5 minutes at room temperature. Following the carbodiimide activation reaction of the acrylic surface graft, the strip 60 and graft are immersed in a 0.02 M MES buffered solution containing 0.5 mg/ml collagen at a PH of 4.0-4.5. The collagen attachment or immobilization reaction is allowed to continue for 20 to 24 hours. The collagen immobilized strip or layer 60 is then triple rinsed in deionized water, then rinsed in a 0.15 M NaCl solution and then a final deionized water rinse. Additionally the collagen immobilized strip or layer 60 can be dried at room temperature above anhydrous CaSO4. Thus it can be seen that "chamber 90" is merely representative of the process.

Following the collagen immobilization in chamber 90 the strip 60 and associated acrylic surface treatment with immobilized collagen is directed to a station or chamber 100 for heparin 104 application using tensioning or tensioner rolls 102. In chamber 100, NAD (nitrous acid degraded) heparin will be coupled in a 0.5M NaCl solution adjusted to pH=4 to the collagen surface. This will take place in about two hours at about 55 degrees centigrade.

The above described heparin application process yields an improved bioactivity of the resultant surface bound heparin. Specifically the bioactivity is determined by measuring either the ability of the immobilized heparin to bind ATIII or the ability to deactivate thrombin. These are expressed in terms of ATIII bound per surface area or thrombin deactivated per surface area. The above process yields an immobilized heparin with an ATIII binding of at least 2 pmol/cm$^2$, and preferably at least 4 pmol/cm$^2$. The above process yields an immobilized heparin with a thrombin deactivation of at least 0.2 IU/cm2 or preferably at least 0.4 IU/cm$^2$. These amounts are believed to be sufficient to have an effective surface for controlling tissue adhesions in the prosthesis of the invention.

The above described collagen immobilization process provides a uniform pure collagen level as shown in FIG. 8. Other known collagen attachment techniques result in the immobilized collagen 97 coupled randomly in the grafted surface as opposed to the above described process where the immobilized collagen 97 is uniformly on the top of the layer 60 (110 after heparin attachment in FIG. 2). The uniformity of collagen attachment with this method is confirmed by surface analysis techniques such as XPS and TofSIMS.

Increasing the purity and uniformity of the top layer of collagen improves the biological response of the resultant prosthesis.

Following the heparin attachment the strip with immobilized collagen and heparin is a semi-finished mesh layer 110 that is rolled onto a mandrel. It should be apparent that where surface treatment is desired over the whole final mesh then the mesh 110 is the finished product. The mandrel may be powered to pull the strip 60 through the radical grafting at chamber 70, hydrolysis at 80, collagen attachment at 90 and heparin attachment at 100. This is merely a schematic representation of the semi-continuous process for illustrative purposes. In practice each step will likely have one set or several sets of feed rolls and pick up rolls, which are not illustrated for simplicity.

One preferential embodiment of the present invention is synthetic hernia mesh prosthesis having surface treatment for controlling tissue adherence on only one side of the synthetic hernia mesh prosthesis. FIG. 2 illustrates one cost effective method of forming such mesh in accordance with the present invention. Specifically as shown in FIG. 2 a semi-finished mesh 110 can be combined with a cleaned mesh 30 that has no surface treatment to form a two layer mesh 130 with surface treatment only on one side, namely the side of layer 110. In connecting the mesh layers 30 and 110 each layer is directed over tensioner rolls 112 to a layer attachment chamber 120 including coupling rolls 124 which may be pressure rolls. Thermo-bonding, pressure bonding, and/or suitable bonding agent or adhesive may be utilized to couple the layers 30 and 110 together. Additional fastening mechanisms could be implemented such as mechanical stitching to secure the layers 30 and 110 if desired, but it is not believed that such additional attachment devices would be required. Tension rolls 122 lead the coupled layered mesh 130 to the mandrel for winding up the finished mesh. The use of a treated layer 110 and an untreated layer 30 for forming the final mesh 130 is a cost effective method of surface treating only one side thereof. Further this process allows great flexibility in selecting the overall parameters of the mesh including thickness, strength, density and the like. The untreated mesh 30 and the treated mesh 110 need not be selected to be identical beginning substrates to yield greater flexibility in final mesh configuration, for example individual layer density and pore size can be varied to better adapt each tissue facing side of the prosthesis to its intended purpose. Further it is contemplated that a plurality of untreated layers 30 could be utilized in the final mesh 130, if desired, but from a practical matter two sufficiently selected layers 110 and 30 should be adequate.

The above described process works well for monofilament polypropylene and monofilament polyester and would work in a similar manner with multi-filament polypropylene and multifilament polyester meshes. Further the multi-filament polypropylene and multifilament polyester meshes are believed to provide greater biocompatibility to the process as well as yielding the better material properties to the mesh. Further the above described surface treatments do not have negative issues with treating multi-filaments as would some prior art surface treatment techniques.

FIG. 3 schematically illustrates a synthetic hernia mesh prosthesis production line for surface treating one side of a synthetic hernia mesh prosthesis formed of polypropylene or polyester mesh with a collagen or heparin surface treatment in accordance with one embodiment of the present invention. The synthetic hernia mesh prosthesis production line and associated process of FIG. 3 is identical to that of FIG. 2 described above except that following hydrolysis the mesh 60 and associated radical graft is directed to only one of the collagen application 90 or the heparin application 100. Thus the synthetic hernia mesh prosthesis production line and associated process of FIG. 3 is essentially utilized to form polypropylene or polyester mesh with heparin surface treatment to control tissue adhesions on one surface thereof, and polypropylene or polyester mesh with collagen surface treatment to control tissue adhesions on one surface thereof. With regard to the use of collagen surface treatment to control tissue adhesions, the method of attaching the collagen of the present invention provides a uniform collagen layer as discussed above which is believed to yield superior tissue adhesion control advantages in the associated hernia repair mesh.

FIG. 4 schematically illustrates a synthetic hernia mesh prosthesis production line for surface treating one side of a synthetic hernia mesh prosthesis formed of polypropylene or polyester mesh with a siloxane surface treatment in accordance with one embodiment of the present invention. FIG. 4 illustrates a mesh cleaning station 20 the same as described above.

FIG. 4 illustrates an alternative method for forming surface treatments on only one side, namely masking one side of the mesh 30. Following cleaning the mesh 30 is coupled to a positive mask 135 with the respective webs or strips lead over tension rolls 32 and 142 to coupling pressure rolls 34 for attaching the positive mask 135 to the mesh layer 30. The coupling of the mask 135 need only be sufficiently strong to be maintained through the surface treatment process which allows a wider variety of attaching techniques to be utilized than considered with attaching layers 110 and 30 described above. The masked mesh layer 140 is wound on a mandrel 140 as shown.

In plasma chamber 40 of the embodiment shown in FIG. 4 of the present invention, the masked polyester or polypropylene mesh 140 is coated with a polysiloxane. The details of the plasma chamber 40 are noted above. The masked polyester or polypropylene mesh 140 is exposed to a reactive gas containing siloxane functional groups, introduced into the chamber 40 from supply 52, and plasma energy to yield a plasma-deposited polysiloxane surface on the masked polyester or polypropylene mesh to form the treated mesh 160 that is wound on an end mandrel. The stream of gas is fed into the chamber 40 from supply 52 and may include, for example, hexamethyldisiloxane and/or tetramethyldisiloxane.

The plasma-deposited surface comprises a polymeric layer deposited onto the masked polyester or polypropylene mesh. Siloxane molecules are fragmented in the plasma phase and recombine to yield a high molecular weight polymeric compound that deposits as a film on the masked polyester or polypropylene mesh surface. The structure of the deposited film depends on the stream gas chemistry and the treatment conditions. Films deposited by this plasma process are, typically, highly cross-linked, pin-hole free, homogeneous, and show good adhesion to the device. Following cessation of the high frequency voltage from supply 48 applied between the electrodes 44 and 46, the gas stream flow from supply 52 may be continued in the chamber 40 in order to quench the masked polyester or polypropylene mesh.

As possible alternatives the polysiloxane application step may be accomplished contacting the masked polyester or polypropylene mesh 140 with a polysiloxane in a liquid carrier, such as via brushing, dipping (immersion), flow coating, spraying and the like. Immersion may include stirring or other agitation of the coating composition, by use of a stirring device or by movement of the substrate to be coated through the composition. However plasma deposition in chamber 40 of the polysiloxane onto the masked polyester or polypropylene mesh 140 is believed to yield a preferential resulting treated surface.

Following the application of the polysiloxane onto the masked polyester or polypropylene mesh 140, the positive mask or used mask 170 is removed by directing the treated mesh 160 to a stripper roll 162 and associated stripper guide or blade 164. The used mask 170 can be wound on mandrel around rolls 172 to help facilitate the process as the mandrel can assist in pulling the layer through the mask removal. Following removal of the used mask 170 the treated mesh 160 can be directed through a final wash 184 via associated rolls 182. The final wash 180 may actually be a series of washes and drying segments as desired. The final polyester or polypropylene mesh 190 treated on one side with polysiloxane is shown wound on a mandrel. The plasma deposited polisiloxane surface is believed to serves as an effective barrier preventing unwanted tissue adhesion without affecting the other properties of the mesh 190.

The positive mask approach shown in FIG. 4 is not limited for use with the siloxane treatments of this embodiment but could also be utilized with the heparin and/or collagen treatments of FIGS. 2-3 in place of the multiple layer formulation shown therein. Similarly the multiple layer formulation shown in FIGS. 2-3 to form a one sided prosthesis could also be used with the siloxane treatment prosthesis of FIG. 4. The positive mask approach is not limited to one that must be peeled off, but can include those that are chemically removed, provided the mask and associated removal chemistries do not affect the treated prosthesis. A simple "positive" mask is shown in which those areas of the mesh 30 not desired to receive subsequent surface treatment are masked off. Negative masking may also be appropriate, in which, for example, an initial "negative" mask is applied to those areas in which subsequent surface treatment is desired and then a second "positive" mask, typically a more conformal application, is applied to the entire masked mesh, followed by a removal of the initial negative mask leaving a final "positively" masked mesh 140 for subsequent treatment.

FIG. 5 schematically illustrates a synthetic hernia mesh prosthesis production line for surface treating one side of a synthetic hernia mesh prosthesis formed of polypropylene or polyester mesh with a siloxane and heparin surface treatment in accordance with one embodiment of the present invention. This process is substantially the same as discussed above in connection with FIG. 4 including the mesh cleaning 20, mask 135 application to form a masked mesh 14, polysiloxane deposition in chamber 40 to form a treated mesh and used mask 170 removal to yield a final mesh 190. The final mesh 190 in this embodiment is a polyester or polypropylene mesh with plasma deposited polysiloxane and subsequent heparin surface treatment on one side thereof to control tissue adherence.

Following the plasma deposition of the polysiloxane onto the mesh 140 to form the treated mesh 160, the mesh 160 the process of the present invention comprises rendering the polysiloxane surface amino functional such as by contacting the polysiloxane surface with an amino- and/or imino-functional compound for a time sufficient to effect adsorption of the amino- and/or imino-functional compound onto the polysiloxane surface. This is shown schematically in activation chamber 200 with the treated strip or mesh layer 160 weaved around rolls 202 to allow for sufficient exposure to the activating compounds 204. In such embodiments, the amino- and/or imino-functional compound may comprise polyethyleneimine, an amino-functional silane and/or diaminopropane. Examples of suitable amino functional silanes include amino-functional silanes sold as the Dow Corning Z-silane series. Depending on the identity of the compound, it may be present in a liquid carrier, particularly when the compound is an amino-functional silane. After adsorption of the compound 204 onto the surface, any imino-functional groups may be reduced to amino-functional groups by addition of a suitable reducing agent to the liquid carrier.

Alternatively, activation in chamber 200 may comprise exposing the plasma-deposited polysiloxane surface to ammonia or an organic amino-functional gas and to plasma energy to yield an amino-functional plasma-deposited surface. Suitable organic amino-functional gases include amino-functional polysiloxane, diaminopropane, and allyl amine. Further alternatives include application of compound 204 with brushing or spraying, but immersion may be most easily accomplished.

Following the activation of the surface of the polysiloxane in chamber 200, the amino-functional polysiloxane surface is contacted with a heparin compounds 214 in chamber 210 via associated rolls 212 under conditions effective to attach the heparin to the treated mesh 160.

Attachment of the heparin to the amino-functional polysiloxane surface of the treated mesh 160 can be accomplished by any of a number of methods known to those skilled in the art. One particularly preferred method is an oxidation method involving the use of periodate. The heparin is contacted with a periodate in a buffered aqueous solution and allowed to react. This controlled oxidation provides a limited number of reactive aldehyde groups per molecule. The periodate is a water-soluble periodate, preferably, an alkali metal periodate, such as sodium periodate. The amount of periodate used is sufficient to react with no more than two of the sugar units in the heparin molecule (i.e., the basic disaccharide residues constituting the structure of the glycosaminoglycan). If the periodate used is sodium periodate and the heparin used is a commercially available injectable form of heparin (e.g., its sodium salt with activity of 160 units/milligram), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to about 8 can be used. A lower pH (e.g., an acetate buffer at pH 4.5) is preferred if a rapid reaction is desired while a more neutral pH (e.g., a phosphate buffer at pH 6.88) is preferred for a slower reaction with a longer storage life. With the acetate buffer at a pH of 4.5, the reaction should proceed for about 3 hours, while with a phosphate buffer at a pH or 6.88, the reaction should proceed for about 16 hours. If desired, the reacted mixture may then be stored prior to use at about 5° C.

The reacted mixture is diluted and the pH adjusted in order to bring the pH of the diluted mixture 214 to a pH that is favorable for the coupling reaction between the biomolecule and the amino-functional polysiloxane. A mild reducing agent, such as sodium cyanoborohydride, is added to the diluted mixture 214 to effect the reduction of the bonds formed between the reactive aldehyde groups on the oxidized biomolecule and the amine functional groups on the polysiloxane coated on the substrate surface. The treated mesh 160 is immersed in the diluted mixture 214 at a sufficient temperature and for a sufficient time to complete the reaction (i.e., attach the heparin). This time can range from about 30 seconds to about 2 hours at temperatures ranging from about 20° C. to about 60° C. For example, at room temperature (i.e., about 20° C. to about 25° C.), the treated mesh 160 coated with the amino-functional polydimethylsiloxane can be flushed with a solution 214 of heparin over a period of 30 seconds to 5 minutes for effective heparin attachment.

Prior to attachment of the heparin to the amino-functional polysiloxane surface in chamber 210, it may be desirable, as an alternative, to expose the amino-functional polysiloxane surface of the treated mesh 160 to a reactive gas containing acrylic acid and to plasma energy to yield a plasma-deposited polyacrylic acid coating on the surface analogous to the process described in FIGS. 2-3. The acrylic layer is believed to yield particularly effective heparin attachment in the final mesh 190 or 130.

FIGS. 2-5 schematically illustrate the process for generally forming the various prosthetics 130 or 190 of the present invention. FIGS. 6A and B schematically illustrate a final synthetic hernia mesh prosthesis die cutting and sealing unit for use with the production lines of FIGS. 2-5 in accordance with one embodiment of the present invention. Specifically the appropriate mesh roll 130 or 190 is pulled through drive rolls 222 to a die cutter 224 to cut the mesh into individuals units 226 followed by packing/sealing station 228 for packaging of the units 226 into individual sterilizable packages 230. The individual units may be merely rectangular sheets, or may be preshaped for particular applications. The figure illustrates an inguinal hernia mesh shape 226 having an internal keyhole 234 and access slit as well as shaped edge 232 designed to generally conform to the inguinal canal. The particular inguinal hernia mesh shape 226 as shown is illustrated purely for illustrative purposes as the present invention is not limited to any particular mesh shape or design.

When forming the surface treatments described herein it may be beneficial to apply such surface treatments to the edge of shaped prosthesis such as keyhole 234 and edge 232. FIGS. 7A and B schematically illustrate a preliminary synthetic hernia mesh prosthesis die cutting for use with the production lines of FIGS. 2-5 in accordance with one embodiment of the present invention. In such an arrangement the mesh 30 (or mesh 10 before cleaning) can be directed through rollers 31 to a preliminary die cutter 33 to form a preshaped strip as shown in FIG. 7B. The die cutters 33 will effectively cut the mesh into substantially preshaped units 226 having the edge shape 232 and internal keyhole 234 (or other particulars of the mesh) together with "runners" 236 sufficient to maintain the mesh 30' and a continuous mesh. The mesh 30' will undergo subsequent processing as defined above for mesh 30 allowing the exposed edges (except for edges coupled to runners 236) to obtain the designated surface treatment as desired. The final die cutter 224 of FIG. 6 would then merely trim the runners 236.

Other edge protection concepts include selectively applying the mask 235 to be spaced from the edge 232 and keyhole 234 or other area so that the surface treatment "wraps around" select portions of the mesh. In the multilayer mesh configuration, similar edge protection can be accomplished by forming the surface treated mesh shape of treated roll 110 as slightly larger along "protected" edges than the shape of untreated mesh roll 30 to accommodate such edge protection.

The above illustrative embodiments show surface treatment only on one side of the final prosthesis, however it may be desirable to have the designated surface treatment entirely covering the prosthesis. Entirely covering the prosthesis is somewhat easier to implement than single side treatment shown in the drawings and thus is not discussed further herein. Physical examples of selected embodiments of the present invention have been made to review the advantages of the identified surface treatments. For example, a polypropylene mesh (10) having a 0.15 mm diameter monofilament mesh having 0.9×0.6 mm typical pore size, and about 97 GSM density (grams/square meter), Burst strength is 834 kPa, Break Strength of 313 MD and 419 CMD, Break Elongation of 160% MD and 1 10% CMD and a thickness of 0.53 mm, was used to form a polypropylene mesh 110 having a collagen and heparin surface treatment to control tissue adhesion, with this mesh 110 prepared according to the process described in connection with FIG. 2 without attaching the mesh to an untreated mesh 30. Further the same starting mesh 10 was used to form a polypropylene mesh 110 having a collagen surface treatment to control tissue adhesion, which was prepared according to the process described in connection with FIG. 3, and a further example used this mesh 10 to form a polypropylene mesh 110 having a heparin surface treatment to control tissue adhesion, which was prepared according to the process also described in connection with FIG. 3. These samples evidenced the advantages of the surface treatments according to the processes described herein.

Surface Treated Sutures and Staples

The present invention provides for a surface treated suture material or surgical staples. Within the meaning of this application the surgical staples include both conventional U-shaped staples, well known in such devices as EEAs and GIAs and similar devices, surgical clips that are essentially staples that do not penetrate the tissue and surgical tacks which are typically single post tissue penetrating members. Both suture material and surgical staples can be categorized as surgical closing members.

As discussed above a concern for all surgical procedures is a lack or minimization of visible scarring. This is particularly true in areas of elective or cosmetic surgery where such issues become paramount. Again, surgical practices have evolved considerably to minimize or hide scars from elective surgical procedures and various topical treatments have come to market which aim to reduce existing scars. Still, few products aim to actively inhibit scar formation at the extracellular level in the earliest stages of wound healing. Fundamentally, scaring is the result of the body's rapid response to a wound, and a natural part of the healing process. Fibroblasts accumulate and proliferate in the wound site and hurriedly generate extracellular collagen matrix to strengthen the wound and allow for migration of cells. The resulting collagen matrix is dense and unorganized, unlike that of the native dermis and characteristic of scar tissue. Conversely, most mammalian fetuses can heal cutaneous wounds in early gestation without visible or histological evidence of scarring. Adult and fetal dermal tissues differ in many ways, but most relevant to wound healing are markedly different expression levels of tissue growth factor beta (TGF-β) and the proteoglycan decorin.

Decorin is a protein that in humans is encoded by the DCN gene. Decorin is a proteoglycan that is on average 90-140 kilodaltons (kD) in molecular weight. It belongs to the small leucine-rich proteoglycan (SLRP) family and consists of a protein core containing leucine repeats with a glycosaminoglycan (GAG) chain consisting of either chondroitin sulfate (CS) or dermatan sulfate (DS). Decorin is a small cellular or pericellular matrix proteoglycan and is closely related in structure to biglycan protein. Decorin and biglycan are thought to be the result of a gene duplication. This protein is a component of connective tissue, binds to type I collagen fibrils, and plays a role in matrix assembly As background on decorin and scar formation see the 1998 study "Decorin Attenuates Gliotic Scar Formation in the Rat Cerebral Hemisphere" by Ann Logan of the Department of Medicine, University of Birmingham, Andrew Baird from SelectiveGenetics Gene Therapeutics, and Martin Berry of Department of Anatomy and Cell Biology, AGKI (Guy's Campus), London published in Experimental Neurology 159, 504-510 (1999). See also the article "Deep Dermal Fibroblasts Refractory to Migration and Decorin-Induced Apoptosis Contribute to Hypertrophic Scarring" by Dariush Honardoust, PhD, Jie Ding, PhD, Mathew Varkey, MSc, Heather A. Shankowsky, RN, Edward E. Tredget, MD, MSc, FRCSC in the Journal of Burn Care & Research published December 2012. Note also it has been supported that the scar suppression capability of a technology that employs a protein delivery mechanism to transport decorin to the wounded tissue in the article "Target-seeking antifibrotic compound enhances wound healing and suppresses scar formation in mice" by Tero A. H. Järvinen and Erkki Ruoslahti in PNAS, Dec. 14, 2010, vol. 107 no. 50 pgs 21671-21676.

While wound healing entails a complex and dynamic series of coordinated biochemical events, transforming growth factor beta (TGF-b) is among the molecules with the broadest spectrum of actions which influence wound healing; in particular TGF-b is the trigger for fibroblast proliferation and collagen generation. In early gestation, cutaneous wounds of most mammalian fetuses heal with no histological evidence of scarring. Fetal wounds heal with decreased TGF-b expression, but the addition of TGF-b to fetal wounds promotes the formation of scars. Given this, the regulation of TGF-b levels in healing tissues is a paramount focus of scar-less wound healing research.

Accordingly, manipulation of TFG-b levels in healing tissues has become a point of focus in scarring and wound healing research. In particular, the proteoglycan decorin binds TFG-b and thereby down-regulates all of its biological activities. Decorin inhibition of TGF-b-regulated fibrosis has been demonstrated in kidney, heart and lung tissues. Decorin is found to have greater expression in fetal versus adult tissues perhaps accounting for the superior fetal wound healing. Conversely, the disruption of decorin has been shown to lead to abnormal collagen fibril morphology and skin fragility, and low-expression levels of decorin are observed in tissue extracts of keloid and hypertrophic scars.

In the field of surgical closure members, the present invention provides bound or immobilized decorin on a surgical closure member substrate. Polypropylene represents one of the most common materials for forming non-absorbable sutures. Decorin and heparin are both polysaccharides and decorin may be immobilized onto the polypropylene suture substrate in the same manner as shown in FIG. 3 and described above in connection with hernia mesh, wherein the reels or rolls of mesh product are replaced with reels, rolls or spools of polypropylene suture material and the decorin binding replaces the heparin binding. In FIG. 3 with suture material there is generally no need for a multi-layer attachment and product 110 will represent the finished product, however it may be desired to combine a single surface treated suture filament with one or more untreated suture filaments to form a multi filament suture and there could be an analogous final coupling step.

Attaching the decorin to a polypropylene suture material could follow the process outlined in FIG. 2 discussed above in connection with hernia mesh with the decorin substituted for the heparin and the suture strand material substituted for the described mesh. This embodiment would yield a polypropylene suture material with immobilized collagen and decorin, providing the advantages of both collagen and decorin to the final suture.

Additionally the attaching of the decorin to a polypropylene suture material could follow the process outlined in FIG. 5 discussed above in connection with hernia mesh with the decorin substituted for the heparin and the suture strand material substituted for the described mesh. This embodiment would yield a polypropylene suture material with immobilized polysiloxane and decorin, providing the advantages of both siloxane and decorin to the final suture. The siloxane may provide desired mechanical properties to the suture material.

The above surface treated non-absorbable suture material is described in connection with polypropylene, a common suture material. The process is substantially identical for a variety of known non-absorbable suture substrates including nylon suture material substrates, Polyvinylidene fluoride suture material substrates polyester suture material substrates, silk material suture material substrates and even stainless steel and titanium suture material substrates (which are used in sternum closure and orthopedic applications). However some of these substrates may require alteration of the activation chemistry, as will be understood by those having ordinary skill in the art following the details of this application.

The decorin surface treated suture material according to the present invention is not limited to non-absorbable suture material but is equally applicable to absorbable suture materials. Absorbable suture materials include the original catgut as well as the newer synthetics polyglycolic acid, polylactic acid, polydioxanone, and caprolactone. The above described processes can be used with these substrates to create a decorin immobilized of bound suture material. Further, some of these substrates as well may benefit from using a collagen then decorin coupling system similar to that outlined in FIG. 2 for mesh.

An alternative attachment processes for decorin/fibromodulin on suture or staple substrates is: 1) Introduce a functional group on the biomaterial surface, e.g. carboxyl functional group; 2) Activate carboxyl functional groups with EDC (1-Ethyl-3-[3-dimethylaminopropyl]carbodiimide) which couples carboxyl groups to primary amines; 3) Incorporate a diamine spacer molecule to produce end point attachment; 4) Expose the amines on the surface or bulk collagen to the carboxyl groups in the GAG of the decorin/fibromodulin and effect the coupling process by adding EDC and NHS(N-hydroxysulfosuccinimide). Another option would be the periodate process: 1) Introduce a reactive aldehyde group in the GAG decorin/fibromodulin polymer backbone using sodium periodate oxidation; 2) Effect the coupling with the spacer amine group via sodium cyanoborohydride reduction.

The decorin surface treatment for surgical closing members includes treatment of staple material. Stapling is often considered much faster than suturing by hand, and also considered to be more accurate and consistent. In bowel and lung surgery, staples are primarily used because since staple lines are more consistent, they are less likely to leak blood, air or bowel contents, still, several randomized controlled trials have shown no significant difference in bowel leakage after anastomoses performed either manually with suture by experienced surgeons, or after mechanical anastomoses with staples.

Although most surgical staples are made of titanium, stainless steel is more often used in some skin staples and clips. Synthetic absorbable (bioabsorbable) staples are also now becoming available, based on materials such as polyglycolic acid and other materials that also form many synthetic absorbable sutures. Thus the decorin may be bound to the staple substrates in the same manner as the analagous suture material discussed above, including the optional use of collagen (FIG. 2) or siloxane (FIG. 5) discussed above, however the staple material will not be in a spool-able format changing the implementation of the particular process steps, mainly to a complete batch processing arrangement. The plasma deposition for staple substrates will likely require substantial product support fixtures supporting a "rack" of staples (forming a batch) simultaneously within the electrodes to allow for a scalable process.

The biomolecule coupled according to the present invention need not be decorin as discussed above. Thus the suture or staple can be surface treated according to the present invention to include a wide variety of bioactive molecules such as those listed above. Examples of biomolecules that may be attached to the surface of the suture material or staple include antibacterial agents, antimicrobial agents, anticoagulants, antithrombotic agents, platelet agents, anti-inflammatories, heparin, enzymes, catalysts, hormones, growth factors, drugs, vitamins, antibodies, antigens, nucleic acids, dyes, a DNA segment, an RNA segment, protein, and peptides.

The bioactive surface treated sutures and staples according to the present invention provide, preferably, immobilized bioactive molecules on the sutures and staples that are provided to promote healing, reduce inflammation and minimize scaring. The attachment of the biomolecule is tailored to improve bioavailability by ensuring exposure of active sites. Surface architecture can be further designed to induce tissue healing, eg. Collagen texturing or glycocalyx-like graft.

Immobilizing the decorin or other bioactive molecule on the surface of the suture material or the staple is preferred, however formation of the coupling to be eluting the biomolecule is also within the scope of the present invention.

Metal staples, such as titanium, stainless steel and the like can also be treated in accordance with the present invention to reduce inflammation, control and promote healing and minimize scaring in accordance with the general flow shown in FIG. 9. The process will start with a clean metal staple surface at step 200. Conventional cleaning steps may be utilized to remove debris and contaminants from the surface. In the manner discussed above the present invention will covalently bind a layer of siloxane to the metal surface as a root layer in step 202. Step 204 shows that the present method proposes to grow a hydrogel graft by polymerizing to the pendant vinyl groups of the siloxane root layer or a silane root layer (note: the present invention contemplates loading the gel component with desired components such as antibiotics). Step 206 defines that the present method contemplates that on this hydrophilic graft covalently bind using a polyamine and then at step 208 Polymers (which includes non-biologics and biologics such as factors, GAGs, heparin, etc) can be then covalently coupled on the polyamine.

In the above discussion silane may be preferable to a siloxane. Silanes are small usually only one Si atom molecules used to form coupling agents or functionalizing agents such as amino, thio, epoxy, or carboxyl function silanes that use Si—H or Si—OCH3 groups to couple to surfaces. Siloxanes are larger oligomers containing Si—O—Si building blocks. However both are operational in the present invention.

Figure 10:
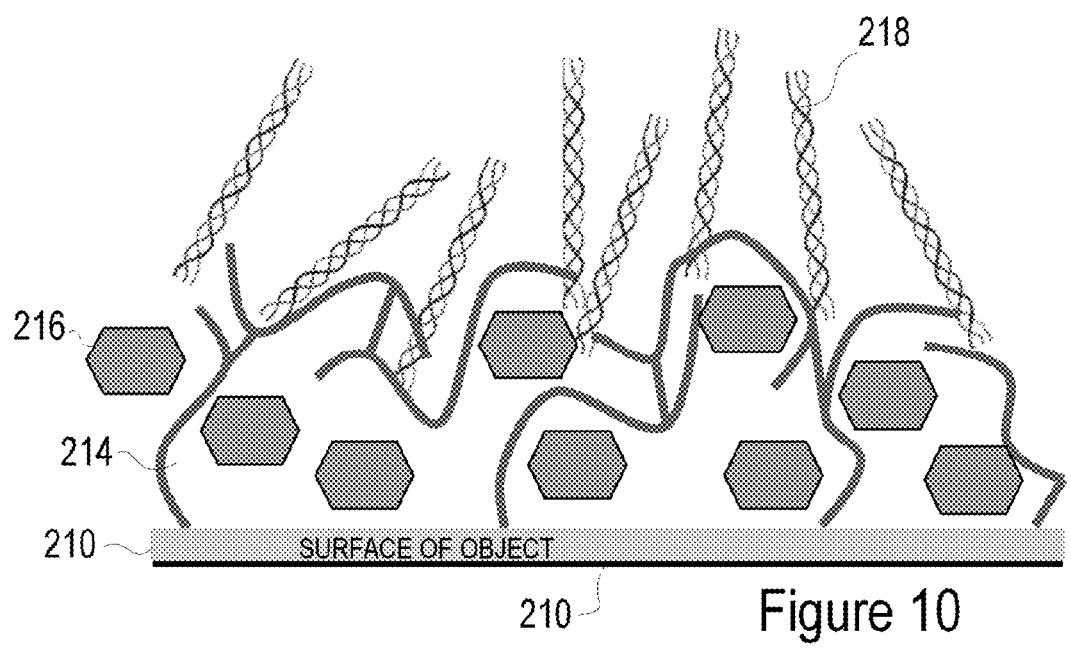
FIG. 10 schematically illustrates the uniform collagen attachment in the synthetic substrate formed in accordance with one aspect of the present invention.

The present invention provides a method for modifying the surface of an object, such as a staple or a suture to impart desired physical architectures and chemical characteristics, such as regenerative conductance, tensegrity, bioactivity, biocompatibility, biofunctionality, cytocompatibility, hemocompatibility, lubricity, hydrophilicity and hydrophobicity, with the resulting surface treated member schematically shown in FIG. 10. The method comprises the general steps of: a) cleaning the surface 208 of the object; b) introducing an active "initiator" layer 210 by exposing the object to a plasma, e.g., a propene or silane plasma; c) polymerizing a hydrogel graft 214 from the initiator layer using a combination of homo- or comonomers; d) impregnating the hydrogel graft with pharmaceutics, biologics, factors, proteins, antibiotics, etc. . . . shown generally as 216; e) If desired, functionalizing, e.g., amino functionalizing, the hydrogel graft to couple biologics, factors, sugars, etc; d) If desired, covalently coupling a biomaterial scaffold (collagen, chitosan, polymers, etc) onto the hydrogel graft to provide a cellular architecture 218 with regenerative conductance to invite cellular ingrowth and host tissue integration.

Figure 11:
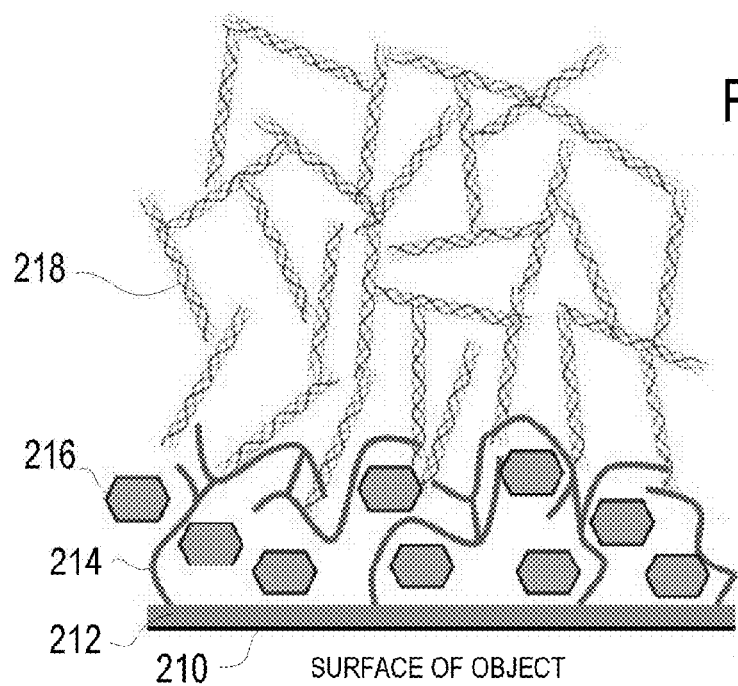
FIG. 11 schematically illustrates the uniform collagen attachment in the synthetic substrate formed in accordance with one aspect of the present invention.

In the field of staples in can be possible to form a "Spontaneous Healing Interface" on the staple with the present invention to form a structure schematically shown in FIG. 11. The above described surface treatments form what can be thought of as a two dimensional surface treatment, but the surface technology can evolve from this effective two dimensional "surface" to a more effective three dimensional scaffold interface 218 of FIG. 11. FIG. 11 represents a collagen "3-D scaffold interface" attachment t layer 218 for staples. The collagen scaffold 218 will be at least 10 microns thick with pore sizes of 2 microns which will allow the scaffold to act as a chemical and physical equivalent to host extracellular matrix. This scaffold 218 will allow the host tissue cells to rapidly generate tissue in-growth without wasting time forming a new extracellular matrix, thus creating a spontaneous or rapid healing interface.

Surface Treated Dental Floss

The present invention provides for a surface treated dental floss. The mechanical handling and processing of such surface treatment is similar to sutures described above and is applicable to the reel to reel batch processing of the webbed prosthetic material for hernia mesh and the like discussed above. As background a number of material has been proposed to be coupled to conventional dental floss. For example one company marketed a ptfe based floss soaked in chlorhexidine, while another commercial endeavor dipped the material in silver nitrate. Breath fresheners, anti-cavity ingredients, and a variety of anti-septics have been proposed for coupling to a dental floss, but no proposal has yielded a convenient method of coupling the desired coating. Most of the prior art proposals will have the material largely eroded from the surface during material handling of the floss. The surface treatment of the present invention allows a secure method of cost effectively coupling any of these desired materials as a bonded surface treatment to the floss. Although any desired biomolecule surface coating may be bonded to the floss with the method of the present invention, Polyhexanide (polyhexamethylene biguanide, PHMB) is deemed to be a first choice. PHMB is a polymer used as a disinfectant and antiseptic. The coupling methodology will follow the above description for hernia mesh of similar substrates.

The preferred embodiments described above are illustrative of the present invention and not restrictive hereof. It will be obvious that various changes may be made to the present invention without departing from the spirit and scope of the invention. The precise scope of the present invention is defined by the appended claims and equivalents thereto.

What is claimed is:

1. A method of treating the surface of a surgical closure device with a biomolecule comprising the steps of:
    a) providing a polyolefin substrate forming a medical device;
    b) cleaning the polyolefin substrate;
    c) exposing the polyolefin substrate to a reactive gas containing siloxane functional groups and plasma energy to yield a plasma-deposited polysiloxane surface on the surface of the polyolefin substrate, then exposing the polyolefin substrate to a reactive gas containing acrylic acid and to plasma energy to yield a plasma-deposited polyacrylic acid coating on the polyolefin substrate; and
    d) attaching a biomolecule to the polyolefin substrate following formation of the plasma-deposited polyacrylic acid coating on the polyolefin substrate, and wherein the biomolecule is at least one of an antibacterial agent, antimicrobial agent, anticoagulant, heparin, antithrombotic agent, platelet agent, anti-inflammatory, enzyme, catalyst, hormone, growth factor, drug, vitamin, antibody, antigen, protein, nucleic acid, dye, a DNA segment, an RNA segment, protein, and peptide.

2. The method of treating the surface of a surgical closure device with a biomolecule of claim 1 wherein the biomolecule is heparin.

3. The method of treating the surface of a surgical closure device with a biomolecule of claim 2 wherein the polyolefin substrate is formed of polypropylene.

4. The method of treating the surface of a surgical closure device with a biomolecule of claim 1 wherein the polyolefin substrate forms a surgical closure device in the form of sutures.

5. The method of treating the surface of a surgical closure device with a biomolecule of claim 4 wherein the biomolecule is a growth factor.

6. The method of treating the surface of a surgical closure device with a biomolecule of claim 1 wherein the polyolefin substrate forms a surgical closure device in the form of a surgical staple.

7. The method of treating the surface of a surgical closure device with a biomolecule of claim 1 wherein the biomolecule is decorin.

* * * * *